(12) United States Patent
Smith

(10) Patent No.: US 9,460,700 B2
(45) Date of Patent: Oct. 4, 2016

(54) EQUIPMENT, SYSTEM AND METHOD FOR IMPROVING EXERCISE EFFICIENCY IN A CARDIO-FITNESS MACHINE

(71) Applicant: Kelly Ann Smith, Norwood, NJ (US)

(72) Inventor: Kelly Ann Smith, Norwood, NJ (US)

(*) Notice: Subject to any disclaimer, the term of this patent is extended or adjusted under 35 U.S.C. 154(b) by 282 days.

(21) Appl. No.: 13/792,658

(22) Filed: Mar. 11, 2013

(65) Prior Publication Data

US 2014/0256511 A1   Sep. 11, 2014

(51) Int. Cl.

| | | |
|---|---|---|
| *A63B 71/00* | (2006.01) | |
| *A63B 15/02* | (2006.01) | |
| *G10H 7/00* | (2006.01) | |
| *G06F 19/00* | (2011.01) | |
| *G10H 1/42* | (2006.01) | |
| *A63B 21/005* | (2006.01) | |
| *A63B 71/06* | (2006.01) | |
| *A63B 22/02* | (2006.01) | |
| *A63B 24/00* | (2006.01) | |
| *A63B 22/06* | (2006.01) | |
| *H04M 1/725* | (2006.01) | |

(52) U.S. Cl.
CPC ............ *G10H 7/00* (2013.01); *G06F 19/3481* (2013.01); *G10H 1/42* (2013.01); *A63B 21/0057* (2013.01); *A63B 22/02* (2013.01); *A63B 24/0075* (2013.01); *A63B 71/0622* (2013.01); *A63B 2022/067* (2013.01); *A63B 2022/0682* (2013.01); *A63B 2024/0012* (2013.01); *A63B 2024/0015* (2013.01); *A63B 2071/0625* (2013.01); *A63B 2071/0652* (2013.01); *A63B 2220/52* (2013.01); *A63B 2220/803* (2013.01); *A63B 2220/805* (2013.01); *A63B 2220/806* (2013.01); *A63B 2220/836* (2013.01); *A63B 2225/50* (2013.01); *G10H 2210/076* (2013.01); *G10H 2220/341* (2013.01); *G10H 2220/421* (2013.01); *G10H 2230/015* (2013.01); *H04M 1/7253* (2013.01)

(58) Field of Classification Search
USPC .......................................... 482/1, 8
See application file for complete search history.

(56) References Cited

U.S. PATENT DOCUMENTS

| | | | |
|---|---|---|---|
| 6,227,968 B1 * | 5/2001 | Suzuki .................... | A63F 13/08 434/250 |
| 2008/0201639 A1 * | 8/2008 | Shoman ............. | A63B 71/0622 715/716 |
| 2012/0021873 A1 * | 1/2012 | Brunner ............. | A63B 22/0235 482/9 |
| 2014/0228173 A1 * | 8/2014 | Shaw ................. | A63B 71/0622 482/4 |

\* cited by examiner

*Primary Examiner* — Oren Ginsberg
*Assistant Examiner* — Shila Jalalzadeh Abyan

(57) ABSTRACT

A system, equipment and process to guide a user in the experience of rhythmic exercise. Playback of an audio signal, such as a musical phrase, that has known rhythmic structure (e.g., beat pattern) is accompanied, by non-audio sensory cues such as a light signal or tactical signal (vibration) to mark rhythmic events in the audio playback (such as the beginning and end of playback and/or audio pulses (beats). In addition, equipment is provided to guide the user in performing a GDM (goal directed movement) sequence that is selected to be performed in synch with the rhythm of the audio signal. The user's motion is detected and compared to desired GDM in the selected sequence and also compared to the rhythm of the audio signal. Sensory cues are provided to guide the user in performing the GDM sequence rhythmically. The system may be implemented in cardio fitness equipment including treadmill, AMT and elliptical type exercise equipment.

16 Claims, 9 Drawing Sheets

EQUIPMENT, SYSTEM AND METHOD FOR IMPROVING EXERCISE EFFICIENCY IN A CARDIO-FITNESS MACHINE

BACKGROUND

1. Technical Field

The present invention relates to a system and method of improved exercise through rhythmic cuing using sensors for detecting left and right initiated goal directed movement sequences on a foot platform of a cardio-fitness machine, and a musical phrase having a grouping of beats whereby sound signals in the musical phrase coincide with light emissions that guide the users movement to be detected.

2. Description of the Related Art

Some games use rhythmic motion to advance the process a game. Rhythmic motion is also used to rehabilitate those with movement impairment. Rhythmic exercise is currently popular in indoor cycling to music or floor exercises performed in groups settings. Visual sensory stimuli are most commonly used in the performance of these rhythmic tasks. Either a leader or an instructor of some sort guide participants to base their movements on visuals to perform the exercise correctly in time with music. In other forms of conventional exercise, music combines with movement for motivational and distractive purposes only. Popular running and biking activities that use music to exercise to lack the precision movement that develops rhythmic sensorimotor skill. And gesture based gaming exercise known as exergames opt the user to synchronize motion with moving images—not the music per se. As a result exergaming fails to offer participants a system and method for assimilating rhythmic feedback to guide future performances more precisely during exercise. Using goal directed movement patterns on cardio-fitness machines addresses these issues and creates a new form of exercise that stimulates a discovery of sensorimotor acuity beneficial to overall human health.

SUMMARY

To enable users to experience auditory cues for rhythmic exercise, a motion sensor system and method of rhythmic cuing to perform goal directed movement sequences on a cardio-fitness machine is novel and useful to furthering what is therapeutic and conventional in rhythmic exercise. Recent research has shown that in NMT—neurological music therapy, professionals rehabilitate the movement impaired primarily using the auditory pathways in structured rhythmic tasks that increasingly meet greater performance objectives. The present inventor recognizes that the auditory pathways strengthen rhythmic skills more so than the visual pathways. Auditory stimuli therefore have a greater potential to enhance performance of rhythmic tasks of all sorts.

The object of the present invention of a motion sensor system and method of rhythmic cuing for sensorimotor synchronizing of audible pulses (beats) corresponding to visible cues that guide the users actions to be detected comprises: sensors for detecting left and right initiated goal directed movement sequences on a foot platform of a cardio-fitness machine, and a musical phrase having a grouping of beats whereby sound signals in a musical phrase or a collection of musical phrases such as that composing a song coincide with light emissions that guide the users movement to be detected.

With this system and method, movement of the user is detected in laterally opposite sections of the exercise space provided by a foot platform of a cardio-fitness machine. A right foot is detected by a right sensor having a detection range in a lateral section of a cardio-fitness machine's foot platform and a left foot is detected by a left sensor having a detection range in a section of the exercise space laterally opposite. Right and left movements on and with the foot platform(s) may also be detected by a respective tactile sensor located within the foot platform or may be detected from an alternate location such as the user's shoe.

A method of improving exercise efficiency by facilitating rhythmic exercise through coordinating goal directed movement in a goal directed movement sequence with beat pulses in an audio signal. The method comprising the steps of selecting an audio signal, determining the timing and location of beat pulses in the audio signal and selecting a goal directed movement (GDM) sequence and identifying the GDM and sequence of GDM in the selected GDM sequence. The method further comprises the steps of generating a non-audio (e.g., visual or tactical) sensory cue to indicate the onset of audio play back and initiate audio playback substantially simultaneously with the non-audio sensory cue that indicates the onset of audio play back. During audio playback, the users GDM are detected and stored. Upon completion of the GDM sequence generate a second sensory cue that is distinct from and not dependent on the timing of the non-audio sensory cue generated to indicate the onset of audio play back. Upon completion of audio playback generate another instance of the non-audio sensory cue that was used to indicate the onset of audio play back. The timing of performance of GDM sequence is then compared with timing of beat pulses in the audio signal and provide the user with feedback. The step of comparing the timing of performance of GDM sequence with timing of beat pulses in the audio signal includes the step of comparing the number of beats in the audio signal to the number of GDM in the GDM sequence.

The timing and location of beat pulses in the audio signal is determined by reading data (stored locally or on a network) or using a beat detection engine to extract beat data from a digital music file. A beat detection engine with multiple beat detectors operating simultaneously to extract beat data from a digital music file may be used to provide a multi-faceted rhythm map.

A plurality of motion sensors may be used to detect user GDM associated with the GDM sequence. At least one left sensor and one right sensor may be used so that motion in an exercise space associated with the user's right side may be distinguished from motion associated with the left side. In addition, or alternatively, a time of flight sensing system (such as that now used in video gaming systems, for example) may be used to detect user GDM associated with the GDM sequence. In addition, or alternatively, a plurality of wireless sensors worn by the user (foot wear, athletic apparel or bands) may be used to detect user GDM associated with the GDM sequence. The method may also include the step of detecting foot pressure applied to a foot platform of the cardio fitness machine. Foot pressure data may be useful in determine which foot is the lead foot in a GDM.

The method may include step of operating in expert mode whereby the user's actual GDM as detected by the sensor system during audio playback is recorded and stored as a new GDM sequence.

The invention may be implemented in cardio fitness machines that generates sensory cues to guide users in performing GDM in a GDM sequence in coordination with rhythmic elements of an audio signal. Such machines include at least one movable foot support (in the case of a treadmill) or two moveable foot support platforms (in the case of an elliptical or AMT, for example) that are moveable with respect to one another. A sensor system provides signals that allow the control system to distinguish between right foot movement and left foot movement in a substantially known spatial area. A control system receives signals indicative of user movement and compares the movement pattern to a stored movement pattern.

The control system further includes an audio processor for retrieving audio signals according user preferences, obtaining beat information for the audio signal and decoding and outputting at least a musical phrase using the audio file; A plurality of sensory cue generators that are controlled independently of one another such that a non-audio (light or tactile) cue is generated at the conclusion of audio file playback and another independent sensory cue is generated at the conclusion of the goal directed movement sequence. The sensor system may include a plurality of motion sensors arranged to detect user GDM associated with the GDM sequence at least one of the motion sensors positioned to detect only motion in an exercise space associated with the user's left side and at least one of the motion sensors positioned to detect only motion in an exercise space associated with the user's right side. The system may also include a plurality of pressure sensors arranged to detect pressure applied by a user's foot to a foot platform of the machine, the pressure sensors providing signals to allow the control system to distinguish between right and left foot pressure.

The invention may also be implemented as system for generating sensory cues to guide users in performing GDM in a GDM sequence in coordination with rhythmic elements of an audio signal The system includes a first motion sensor having a range for detecting movement of the user in a direction intersecting a lateral section of a plane surrounding a foot platform of a cardio-fitness machine and a second motion sensor having a range for detecting movement of the user in a direction intersecting a laterally opposite section of a plane surrounding a foot platform of a cardio-fitness machine. The system includes an audio playback system for playing an audio signal having known beat characteristics. The system further includes a non-audio cue generator for generating a first non-audio cue (such as the flash of a light) to correspond with select beat pulses in the audio signal. The select beat pulses may be the first and last beats in a musical phrase or, alternatively, some or all of the beats perceived during playback of the studio signal. The audio signal may be a single musical phrase or more complex musical structures. The system may include an expert mode engine to use system equipment to record the user's GDM as detected by the sensor system during audio playback. The system may include additional sensory cue generators to, for example, generates a second sensory cue independent of the first non-audio cue when a GDM is detected. The system is preferably run by software operating on a general purpose computer that may include special purpose processors. Various software implemented engines may be used to process inputs from system components, the software implemented engines may include a beat data extraction engine, a laser light beam control engine, a gesture recognition engine, a performance assessment engine, a GDM preference engine, an expert mode engine, a MPORG engine, an audio encode, an audio decoder and a recommendation engine.

These and other objects, features and advantages of the present invention will become more apparent upon reading of the following detailed description to the system and methods within the design.

DETAILED DESCRIPTION

Figure 1:
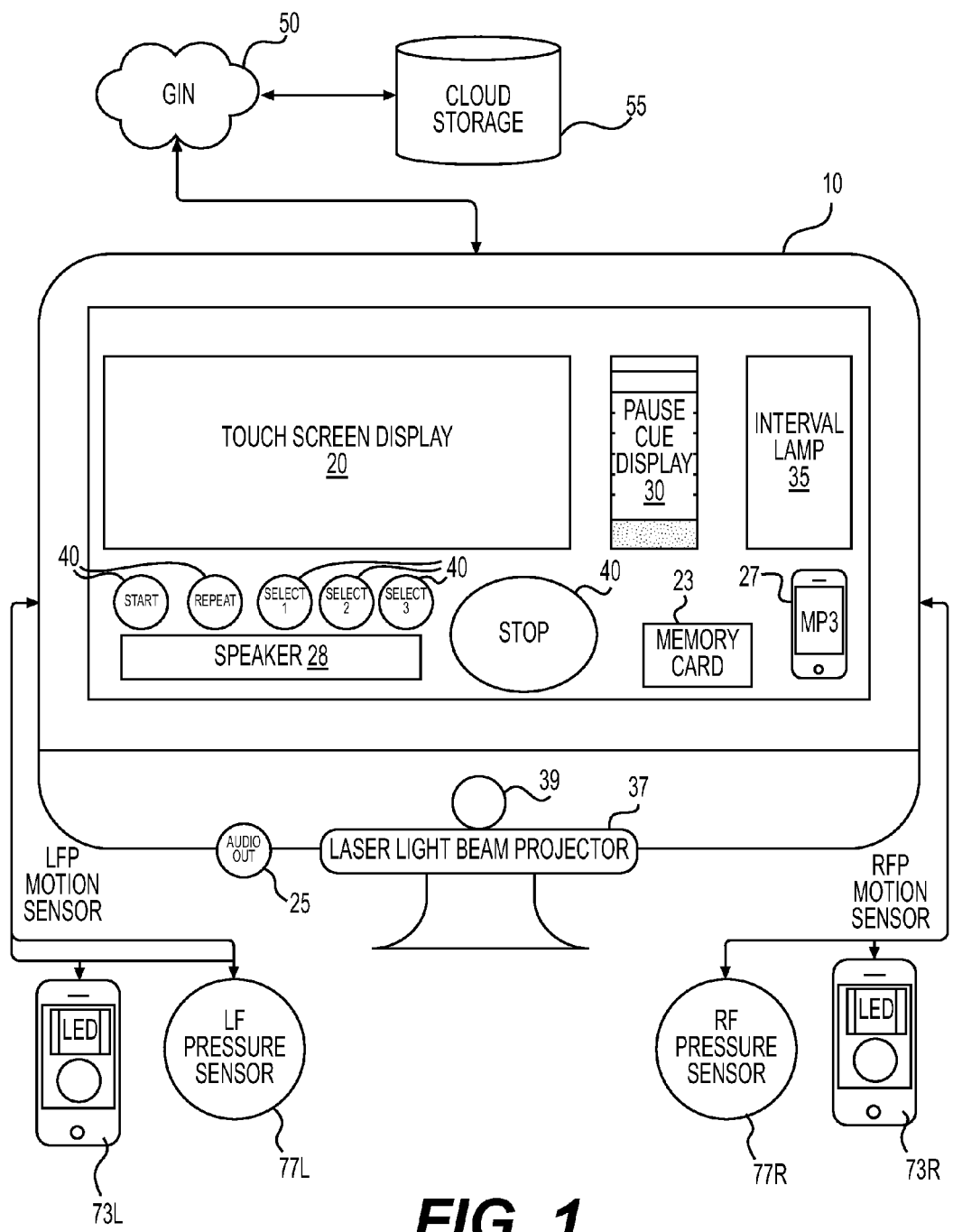
FIG. 1 is a schematic representation of the Control Panel and related hardware of an embodiment of the invention.

FIG. 1 is a schematic representation of the Control Panel 10 and related hardware of an embodiment of the invention. As shown, the Control Panel 10 includes a multi-touch screen display 20, a speaker 28, a pause cue display 30, an interval lamp 35, a laser light beam projector 37, and various user input selection buttons 40 (including a START button, a REPEAT button and a STOP button). The Control Panel 10 has various input and output connections (jacks) for receiving connection to motion and pressure sensors (e.g., 73R, 73L, 77R, 77L) and also includes an audio out connection (jack) 25 to allow a user to connect a headset. Naturally, wireless connections (such as Bluetooth) could be used in lieu of any of the hardwired connections to connect sensors, headphones or other components to the Control Panel 10. Wireless connectivity may be necessary when movement/pressure sensors located on the user (such as in the user's shoes or on the user's clothing) are used instead of sensors attached to the exercise machine.

The Control Panel 10 also includes an audio player dock 27 to allow the user to connect an audio player (e.g. MP3 player, smartphone, tablet etc.) to the control panel. The Control Panel 10 also includes a memory card reader slot 23 to allow a user in insert a memory card containing data such as audio data (music) and/or biographically/user data. Naturally, user devices with wireless communication capability could communicate with the Control Panel 10 wirelessly, if desired.

The pause cue display 30 is preferably a simple easily visible and understood indication of the time remaining until the next interval begins. As shown in FIG. 1, the pause cue display may be a series of lights that sequentially change appearance (color or on/off) from top to bottom to depict the time remaining.

The laser light beam projector 37 may be a simple laser beam flash of a visual cue (described below) or it may be used a projector of the type used to project ("paint") an image onto a surface of the exercise equipment. This is especially useful in the context of a treadmill where the foot platform surface is moving under the user's feet. Laser light beam projector 37 could project visual cues ranging from simple light flashes to lines of demarcation indicative of time intervals associated with beat sequences or Goal Directed Movement (GDM) sequences.

The laser light beam projector comprises a laser projector or scanner 37 controlled by a laser light beam control engine 770. Sophisticated laser projectors now available modulate a laser beam to project a raster-based image. The systems work either by scanning the entire picture a dot at a time and modulating the laser directly at high frequency, much like the electron beams in a cathode ray tube, or by optically spreading and then modulating the laser and scanning a line at a time, the line itself being modulated in much the same way as with Digital Light Processing (DLP). This technology produces the broadest color gamut available in practical display equipment today, because lasers produce truly monochromatic primaries. The laser signal is modulated by introducing the video signal to the laser beam by an acousto-optic modulator (AOM) that uses a photorefractive crystal to separate the beam at distinct diffraction angles. The beam must enter the crystal at the specific Bragg angle of that AOM crystal. A piezoelectric element transforms the video signal into vibrations in the crystal to create an image. Horizontal and vertical refresh is achieved by a rapidly rotating polygonal mirror to give the laser beam the horizontal refresh modulation. The beam reflects off of a curved mirror onto a galvanometer-mounted mirror that provides the vertical refresh. Another way is to optically spread the beam and modulate each entire line at once, much like in a DLP, reducing the peak power needed in the laser and keeping power consumption constant. While this structure produces high quality projected images, other technologies may be more appropriate when cost is taken into account. As a less costly alternative, a laser scanner may be used. Laser scanners consist of small mirrors that are mounted on galvanometers to which a control voltage is applied. The beam is deflected a certain amount, which correlates to the amount of voltage applied to the galvanometer scanner. Two galvanometer scanners can enable X-Y control voltages to aim the beam to any point on a square or rectangular raster. This enables the laser lighting designer to create patterns. Other methods of creating images through the use of galvanometer scanners and X-Y control voltages can generate letters, shapes, and even complicated and intricate images.

A sensor system is provided to detect user movement. The sensor system preferably is able to distinguish between movement of the user's right and left limbs (usually legs and feet) and may also be able to distinguish arm and hand movement and the pressure applied to the foot platform and other parts of the cardio fitness machine. The sensor system may include a time-of-flight camera system and/or an array of motion sensors that detect motion is specific zones of movement. The sensor system my further include pressure sensors for sensing pressure applied to the foot platform of the cardio fitness machine. The presume sensors may be applied on the foot platform, under a treadmill belt or in a user's show. Sensors may also be worn by the user when attached to /embedded in user's apparel, arm bands or shoes.

As shown in FIG. 1, the Control Panel 10 may include a time-of-flight camera system 39 to track user movements. Any known time-of-flight camera system may be used. An embodiment of the time-of-flight camera system may include the following components: Illumination unit (preferable infrared); Optics (a lens arrangement that gathers the reflected light and images the environment onto the image sensor, optical band pass filter only passes the light with the same wavelength as the illumination unit); image Sensor (each pixel measures the time the light has taken to travel from the illumination unit to the object and back); Driver Electronics to control the illumination unit and the image sensor have to be controlled by high speed signals; and a Computation/Interface to calculate distance.

Various sensors may be wired to or otherwise in communication with the Control Panel 10. In the embodiment shown in FIG. 1, left 73L and right 73R motion sensors and left 77L and right 77R foot pressure sensors are connected to the Control Panel 10. The motion sensor heads preferable include both movement sensors and LED lights that can provide a visual cue (as described below).

The Control Panel 10 and sensors 73, 77 are designed to be mounted to a base and placed in proximity to a cardio-fitness machine so that the left and right pliable arms upon which the sensor heads are mounted can be arranged to a suitable position near the foot platform of the cardio-fitness machine and to the constrained path of motion unique to the mechanics of the machine. The motion sensors 73L, 73R are preferably located at the end point of adjustable gooseneck supports attached to the cardio-fitness machine or Control Panel 10. The inner spaces of the tubes of gooseneck are used as cable laying paths for the power cables and signal cables for the motion sensors 73. The number of sensors is not limited to that of this embodiment and may include several provided it can operate in a manner similar in support of the method. The motion sensor 73R has a detection range of the exercise space constrained rightward by the path of motion of the fitness machine's foot platform. The motion sensor 73L has a detection range nearest the left foot platform and the exercise space constrained leftward by the path of motion of the fitness machine's foot platform. Each sensor is integrally provided with a light emitting element (LED) 73Q and a motion sensing (e.g., light detecting) element 73s. When a part of the user's body enters the detection range within the exercise space, light from the light emitting element is blocked and cannot be received by the corresponding light detecting element. Motion detection is realized by detecting such a state. In a mode whereby the lack of detection is made upon the cessation of movement e.g. the lack of the lower extremity entering the range of detection within the exercise space, the unblocked sensor emits a visible signal. The visible signal making realized a light cue for a goal directed movement to be performed.

The foot pressure sensors 77L, 77R may be any known pressure sensor/transducer technology with associated power supply, transmitters and microcontroller. An exemplary embodiment uses a piezoelectric sensor that uses the piezoelectric effect to measure pressure, acceleration, strain or force by converting them to an electrical charge. Piezoelectric sensors may be located on the foot platforms of elliptical or AMT machines and under the moving belt of a treadmill. Sensors may also (or alternatively) be located in the user's footwear using, for example, the Nordic Semiconductor SoC (System-on-chip) design Microchip Technology PIC16F688 microcontroller; 3V Lithium 2032 battery and a 30 mm-diameter piezoelectric sensor.

The Control Panel 10 may include various wireless communication technologies. As described, above Bluetooth may be used for exchanging data over short distances. Wi-Fi or a similar protocol may be used to exchange data over a local or Global Information Network (GIN). In this way, the Control Panel 50 may access data stored in "cloud storage" data bases 55 or over the Internet, which may be beneficial as described below.

Figure 2:
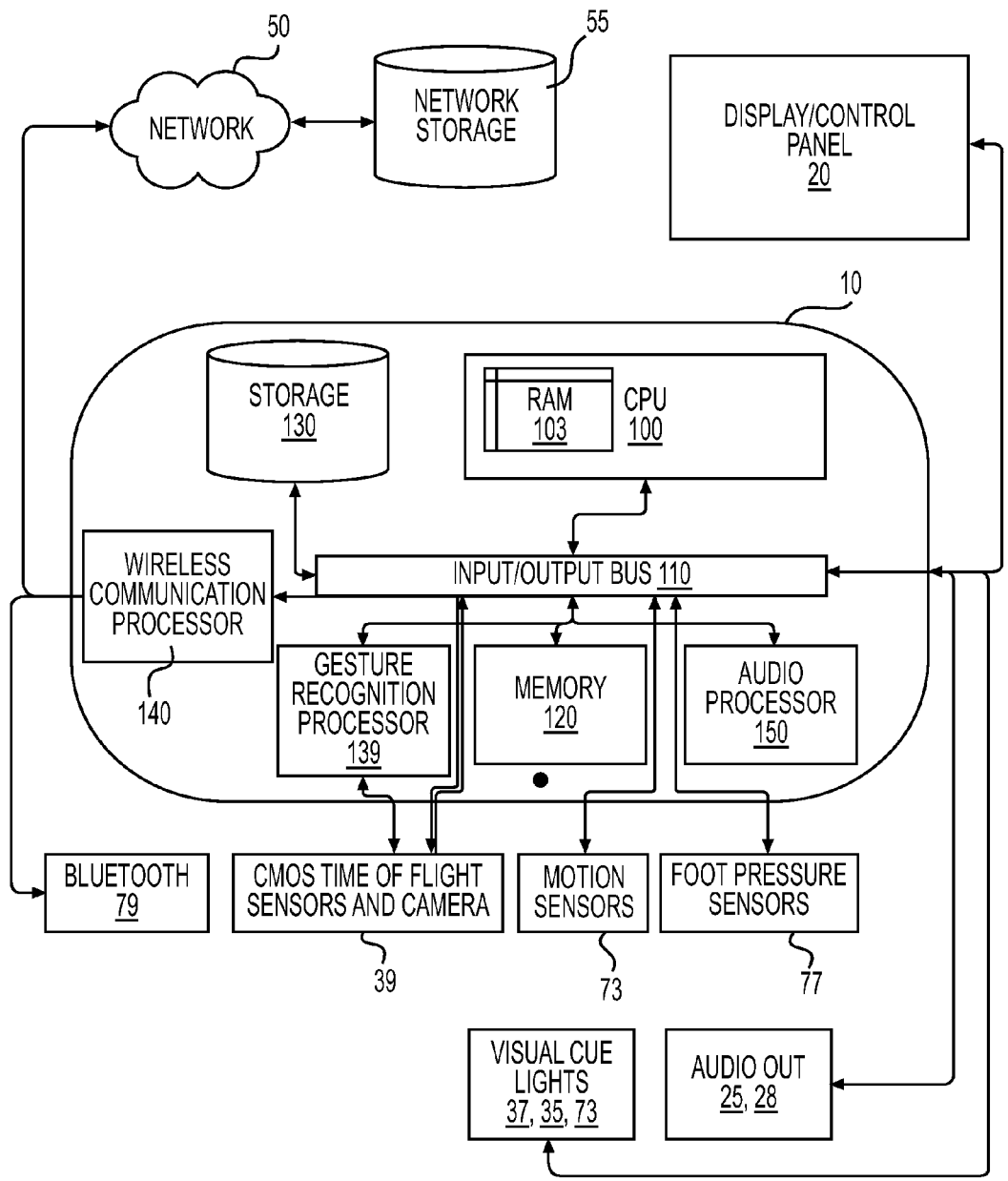
FIG. 2 depicts the System Architecture of an embodiment of the invention.

FIG. 2 depicts the System Architecture of an embodiment of the invention. As depicted much of the hardware is contained within the housing of the Control Panel 10. The hardware includes a CPU 100 with on board RAM 103; an input/output system bus 110 (including control bus, address bus and data bus functionality); system memory 120; system storage 130 (flash or hard drive); a gesture recognition processor 139 (if the system includes time-of-flight sensing capability); and a wireless communication processor for enabling Wi-Fi, Bluetooth and/or other wireless data exchange over a local or global information network 50.

The system also includes an Audio Processor 150 for providing digital audio and beat information to the system. The Audio Processor 150 may include a beat data extraction engine 730 for extraction of beat information from a music sample. The Audio Processor 150 also includes digital audio encoders and decoders as necessary to process music files. Pulse-code modulation (PCM) may be used to encode music as a digital signal. A digital-to-analog converter performs the reverse process, and converts the digital signal back into an audible sound.

Improvements in beat detection will offer more options for a listener to base his impressions on including note onsets, drumbeats and patterns, and harmonic changes. As such, it is possible to expand the concept of what is a beat by including what is not exactly a beat per se, but what humans may perceive a beat to be. Experienced users may do this when extracting beats to match a GDM to. In the digital format, music from a digital (MP3 for example) file can be converted and subdivided into another form of representation. For instance algorithms may achieve such a conversion by locating the number of highest amplitudes corresponding to number of beats in a song and store those instances as values for some sort of future processing. Once retrieved, these values offer location details to formulate a multi-faceted rhythm map. In this format, such a map can be used for several purposes within a system that integrates musical phrases. For instance, a comparison between this map and newly obtained digital information may be understood to have different meaning in a new context. That features of the musical information offer new variables from such data sets is relevant to the present system and method for rhythmic cuing. The present inventor recognizes that as methods become more sophisticated they will match the capabilities of the auditory pathways in retrieving information about sounds in music.

Whereas algorithms look for periodic peaks of a particular feature to represent the beat events in a musical phrase, others will be devised and improve upon current methods of beat detection. A reason for the improvement stems from the amount of variability within the human auditory system and that when listening to music humans form impressions of what a beat is from the multi-faceted representations of information within of a song. Improvements in beat detection will offer more options for a listener to base his impressions on including note onsets, drumbeats and patterns, and harmonic changes. Obtaining sound information at this level will require more than one type of detection to be made at a time. The inevitability of more than a single beat detector launched simultaneously will improve the overall accuracy and experience of a system and method of the present invention. Several monitors aggregating information from multiple detectors would generate a more advanced beat tracking response over an individual detector operating independently. This improvement in digitizing music will benefit usage of the present invention and the ability to achieve the objective of performing goal directed movements in response rhythmic cuing.

As shown in FIG. 2, the Control Panel 10 receives input from Bluetooth 79 and other wireless sources 50; the time-of-flight sensors and camera 39; the motion sensors 73; and the foot pressure sensors 77. The Control Panel may output signals to each of these components and also outputs control signals and engages in data exchange with the visual cue lights 35, 37, 73; the touch screen panel 20 and the audio out sources 25, 28.

Figure 3:
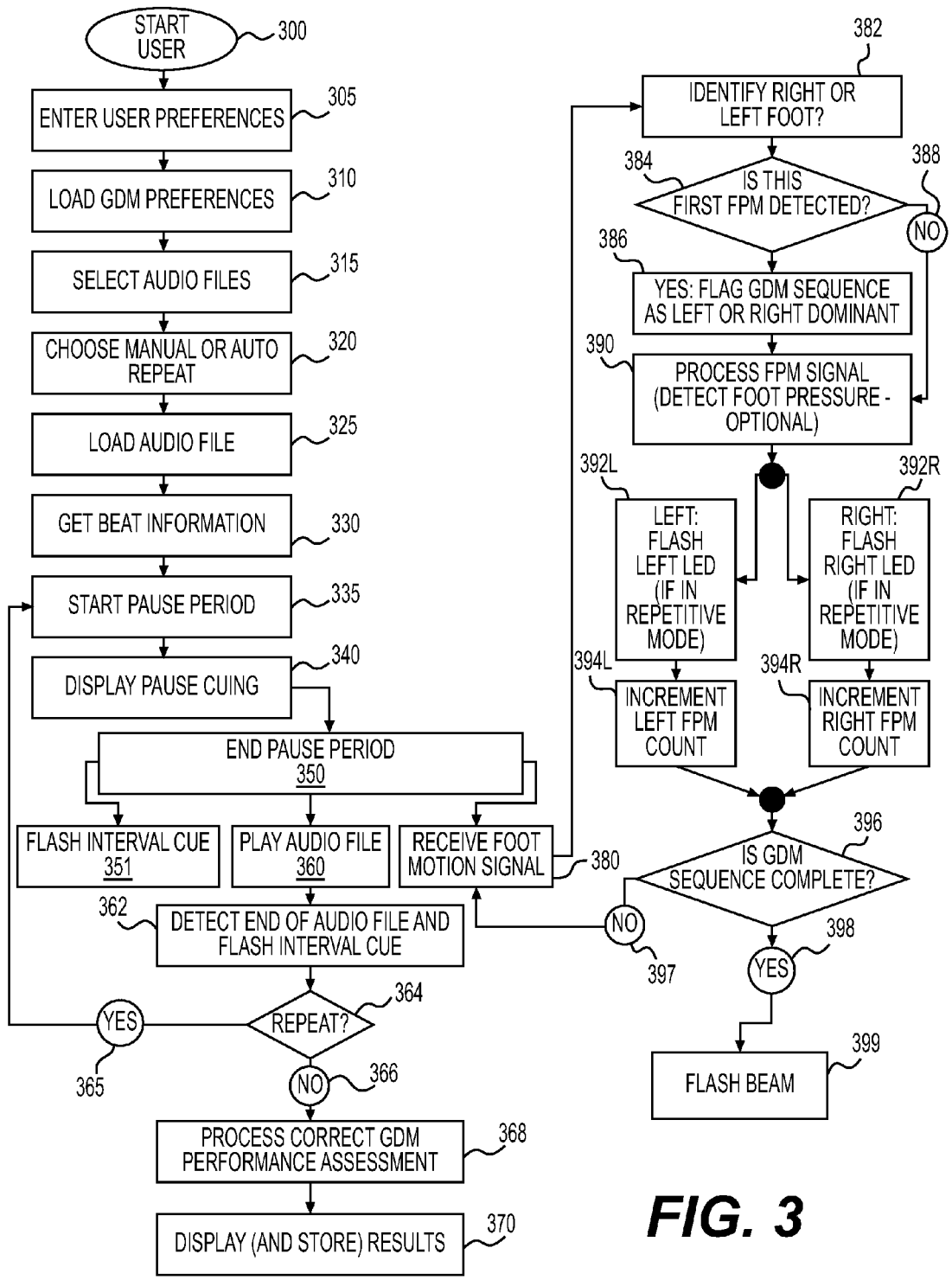
FIG. 3 is a flowchart showing operation of an embodiment of the invention.

FIG. 3 is a flowchart showing operation of an embodiment of the invention. As shown, the process begins with the user initiating the process at step 300 (such as by pressing the start button 40). At step 305, the user enters preferences and other user specific information including for example a USER ID that allows the system to retrieve records from local storage 130 or cloud storage 55. At step 310, the system loads data related to the preferred Goal Directed Movement (GDM) sequence including, for example, the number of GDM in the sequence, the left-right sequence of GDM and, if desired, the spatial orientation of each GDM.

GDM sequences are a set number of GDM's performed in series according to a method suitable to the particular cardio-fitness machine. A pattern of GDM's is comprised of alternating foot movements on and with Fp and its constrained path of motion. For instance, a foot platform on a treadmill belt is the rotating singular rubber belt; an elliptical trainer has pedals that function as a Fp that rotates in tandem; and the Fp of an AMT Adaptive Motion Trainer function in a dual plane of resistance, up and down and back and forth. The number of movements on and with the Fp varies according to the goal directed movement selected and the objectives and preferences unique to the user's performance whereby a same GDM sequence can be repeated and assessed; or the assessments made can be inclusive of various GDM sequences performed according to the entry preferences of the user.

GDM preferences will be reflective of the particular audio file(s) selected and most importantly, the number of beat events in the musical phrase comprising the audio file selection as the objective of achieving the pattern in the GDM sequences is to match GDMs to a beat in the phrase.

At step 315, an audio file is selected. The selected audio file functions as sound content representing the beat events in a musical phrase. The sound information is processed into a set number of beat events, which during the performance of a GDM sequence, guide the user's movements to be coincident with light emissions. PCM information formatted into Mp3 files supplies the content of sound information. The digital information is subsequently reformatted to meet the present invention's requirement for processing i.e., extracting beat information. User preferences for selected audio files will correspond to the user preferences for GDM sequences. Audio files may be obtained in the form of an entire song or as a component of a song i.e. a musical phrase. Audio files can be categorized according to beat event information for the purposes of matching GDM sequences to them and selected on the basis of their compatibility.

At step 320 a selection is made (either manually or from user preferences) as to whether the audio file (musical phrase) will be automatically repeated one or more time or repeated only in response to user input (such as the REPEAT button 40) At step 325, the audio file—preferably representative of a musical phrase—is loaded into the system. At step 330, the system gets beat information with respect to the selected audio file. The beat information may be extracted by the audio processor 150 or obtained from local storage 130 or network storage 55. The beat information includes information as to the number and timing of the beats in the audio file. As noted above in connection with the discussion of the beat extraction engine 730, more sophisticated beat detection/extraction (such as the creation of a multi-faceted rhythm map from the digital audio file) may be used as the technology becomes more readily available.

At step 335 a pause period begins. The duration of the pause period—which is the time between successive playing of the audio file—may be determined based on user preferences, user input or user performance as determined by the system. At step 340, pause cuing is displayed on the pause cue display 30. In the embodiment shown in FIG. 1, a series of eight blocks of light are illuminated and then turned off one by one from top to bottom to cue the user as to the end of the pause period.

At the end of the pause period 350 three things happen substantially simultaneously. At step 351, a flash interval cue is provided to the user. In the embodiment shown in FIG. 1, the flash interval cue is provided by an interval lamp 35 on the Control Panel 10. At step 360, the audio file begins to play and audio output is provided through the audio out jack 25 or through the speaker 28. At the same time, as shown at step 380, the system begins to look for signals from the sensors, e.g., the sensors that monitor the user's foot motion [motion and/or pressure]. An exemplary process of monitoring the user's GDM movement is depicted at steps 380-399 described in detail below.

Briefly, as noted, pause cuing is displayed prior to the onset of audible musical phrase. At end the pause period a first beat in the phrase becomes audible, and is synchronous with a visible signal emitted from the control panel. The signal flashes as an interval cue. The audio file begins to play. The GDM sequence begins. At the end of the audio file, a signal flashes an interval cue lamp 35. If the user preference has instructed the audio file to repeat the audio file, a new pause period starts and the user resumes the performance of a GDM sequence with the foot laterally opposite the one that commenced the previous GDM. A correct GDM sequence performance assessment will be judged according to the user preferences for the number of GDM's in the sequence selected.

The end of the audio file playback is detected at step 362 and a flash interval cue is made using the interval lamp 35. The system then determines if audio file playback is to be repeated (at step 364). If YES (step 365), the process returns to step 335 and the pause period begins. If the desired number of playbacks has been reached or if manual repeat was selected at step 320, the playback ends (step 366) and the system processes a correct GDM assessment at step 368 and proceeds to display and store results at step 370. The results may be stored in local data storage 130, on a memory card reader 23 or in network storage 55.

Steps 380-399 depict one exemplary process of monitoring the user's GDM movement. It should be understood that with the use of enhanced sensing such as the CMOS time of flight sensors and camera 39 and gesture recognition processor 139, it is possible to monitor and assess user performance of GDM with great precision. It is also possible to monitor users GDM performance by applying Bluetooth 79 or other wireless sensors to extremities (in user's apparel or bands worn by users). However, many benefits of the invention are achievable by monitoring a user's foot motion and perhaps foot pressure applied to equipment as described hereinafter.

At step 380, the system receives a foot motion signal. At step 382, the system determines if the foot motion signal came from a right sensor 73R or a left sensor 73L. At step 384, the system determines whether that foot motion signal received is the first foot motion signal of this GDM sequence. In general it is desirable to begin and end each of the GDM sequences according to the present invention with motion of the same foot. Thus, if a GDM sequence begins with left foot movement, it should end with left foot movement. The next iteration of the GDM sequence (after the pause) will then begin with right foot movement and end with right foot movement. Thus, if (at step 384) it is determined that the foot motion signal is the first foot motion signal of the GDM sequence, then the GDM sequences is flagged according to whether the movement was a left foot movement (sensor 73L) or a right foot movement (sensor 73R). If the foot motion signal is NOT the first foot motion signal of the GDM sequence, then step 386 is skipped at step 388.

At step 390, the foot motion signal is processed by, for example, recording its timing, left or right and, optionally, other characteristics such as pressure, velocity, direction, acceleration etc. The foot pressure sensors 77L, 77R or wireless sensors 79 are used for detecting foot pressure while the sensors and camera 39 and gesture recognition processor 139 may be used for detecting other motion characteristics. When a left foot motion signal is detected, the system may flash the Left LED (preferably located on the left sensor head 73L) at step 392L. The system then increments the Left FPM (foot platform motion or foot motion signal) count by one at step 394L. Likewise, when a right foot motion signal is detected, the system may flash the Right LED (preferably located on the right sensor head 73R) at step 392R. The system then increments the Right FPM count by one at step 394R.

At step 396, the system then determines whether the GDM sequence is complete by, for example comparing the number (and possibly sequence) of foot motion signals received to the number of FPM corresponding to the GDM sequence loaded at step 310. Regardless of the precision used to monitor GDM performance, the determination that the sequence is complete is made by comparing specified number of GDM to detected GDM.

Information obtained from the user preferences (at step 305) is used to determine if the GDM Sequence is complete. In correct sequencing, the first and last GDM is detected by a same sensor so that the next performance can begin on the laterally opposite side. However a smooth transition is not always a given. An uneven number of GDMs in a pattern work best for an initial and final detection to be made. In the event there is an even number of GDMs in a pattern, the pause period aids in a smooth transition so that the side laterally opposite can initiate the next GDM.

Interval only GDM sequences are detected by the same sensor twice i.e., one detection for the first beat and one detection for the last beat, at the beginning and end of the musical phrase, initiated by a right or left dominant performance. In the event the music ends, the GDM is complete. If the musical phrase is audible and the GDM sequence resumes after left or right foot motion detection, the number of GDM in the users preferred GDM sequence is not yet achieved and the performance continues according to the method until the music ends.

In repetitive mode, the number of detections is more than two. The number of detections in repetitive mode is always upwards of three i.e., at least one more detection must be made in the pattern of detections other the initial detection and the final detection. According to the method said detections are made by the same sensor. In other words, for every complete left or right initiated GDM sequence performance, the pattern of detection to be made next has the sensor laterally opposite entering a detective state.

At step 397, if the GDM sequence is not yet complete, the system returns to step 380 and receives the next foot motion signal. If the GDM sequence is complete, at step 398, the system proceeds to step 399 and a visual cue indicating the completion of the GDM sequence has been detected is displayed. The embodiment shown, the visual cue is made by flashing a laser beam at step 399 using, for example, the laser light beam projector 37.

By receiving Interval cues only, and if the user preferences specifies manual input of the audio file, a beam will flash to signal that the GDM sequence is completed. Audio files that play repeatedly according to user preferences based on their compatibility with a GDM sequence in use will receive a flash beam after the repetition of the pattern within the selected GDM sequence is complete. If more repetitions of GDM are required by the system to meet the specified user preference the flash beam will not appear until the end of the musical phrase.

It should be recognized that the timing of the flash interval cue of step 362 (signifying the end of audio playback) and the laser beam flash of step 399 (signifying the completion of the GDM sequence) are independent of one another. However, performing the GDM sequence so that these two signals are in (or near) synch is an important user objective of the invention. Moreover, synching the flashing of sensor LED'S 73L and 73R (at steps 392L and 392R) with the beats of the audio signal is indicative of highly desirable rhythmic entrainment. Thus, the system and process described above provide a tool to allow users to exercise rhythmically.

Before describing use of the invention further, embodiments of the invention in the context of several types of cardio-fitness machines will described with reference to FIG. 4 (an adaptive motion trainer); FIG. 5 (an elliptical machine) and FIG. 6 (a treadmill). By virtue of these examples, those skilled in the art will understand that the invention may be adapted for use in other cardio-fitness machines.

Figures 4, 4A:
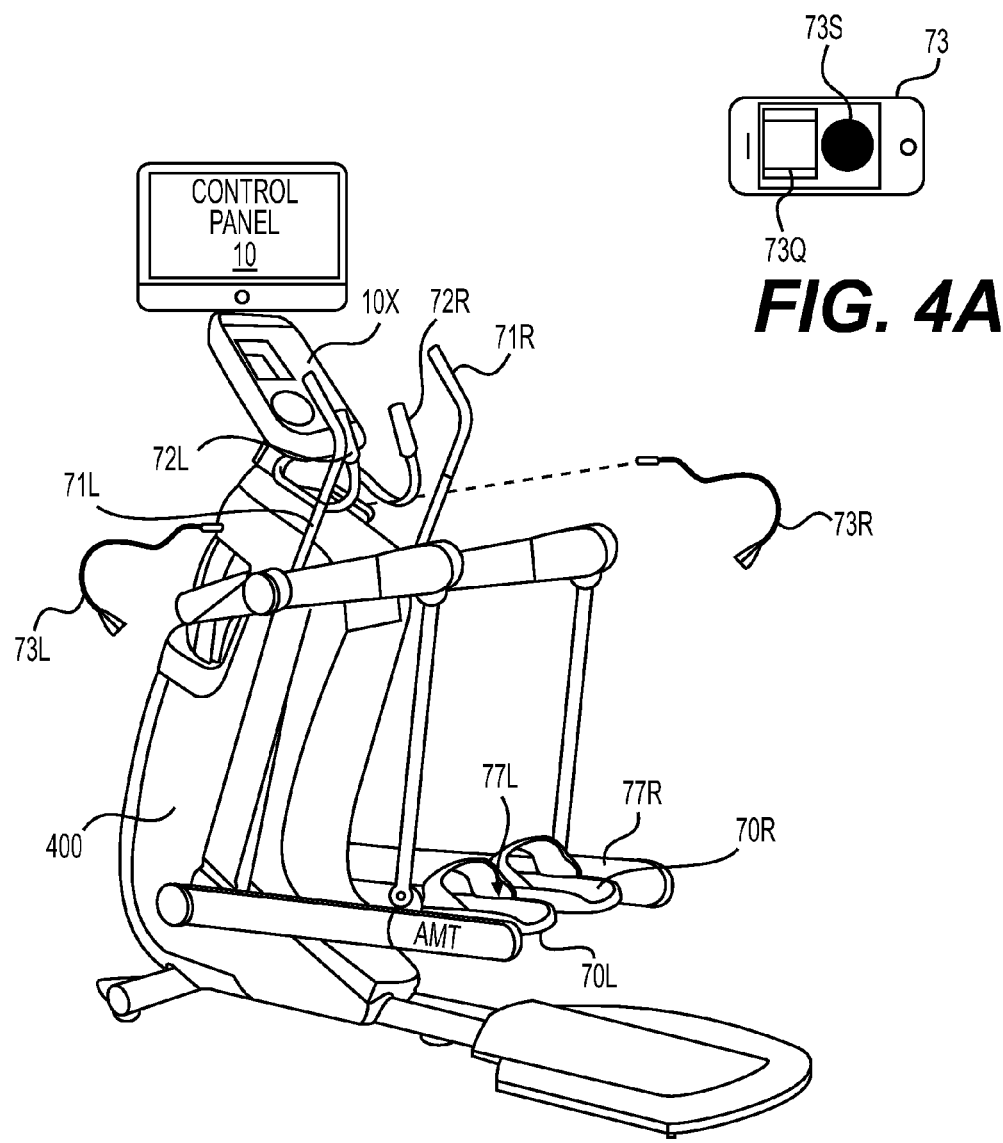
FIG. 4 is a partially schematic perspective view of an adaptive motion trainer [AMT] exercise machine according of to an embodiment of the invention.
FIG. 4A is a schematic view of one form of sensor head according of to an embodiment of the invention.
Figures 5, 5A:
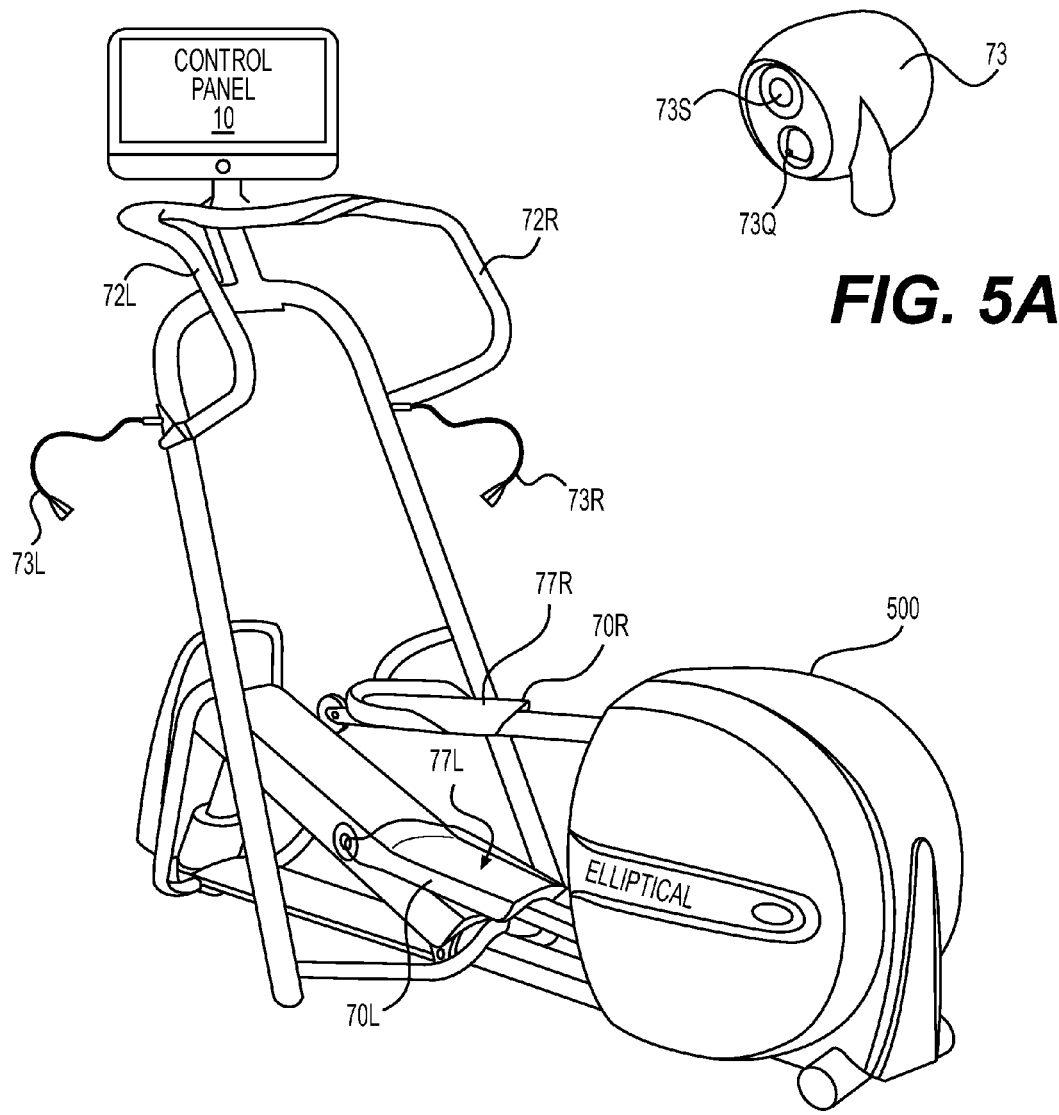
FIG. 5 is a partially schematic perspective view of an elliptical exercise machine according of to an embodiment of the invention.
FIG. 5A is a perspective view of another form of sensor head according of to an embodiment of the invention.

FIG. 4 is a partially schematic perspective view of an adaptive motion trainer [AMT] 400 exercise machine according to an embodiment of the invention. As is known it the art, the AMT body 400 includes mechanical linkages and controls to guide user motion. The AMT further includes a left foot platform 70L and a right foot platform 70R; a left movable arm 71L and a right movable arm 71R; left and right fixed arms 72L, 72R; a left foot movement sensor 73L that includes a head mounted on an adjustable gooseneck support and a right foot movement sensor 73R that includes a head mounted on an adjustable gooseneck support. Foot pressure sensors 77L, 77R are located on the respective foot platforms. A Control Panel 10 of the type described above is provided at a convenient location and the AMT may include additional controls 10x.

FIG. 4A is a schematic view of one form of sensor head according of to an embodiment of the invention. The sensor head includes a motion sensor portion 73s and a LED light 73Q that can be used to provide the left and right flashed of steps 392L and 392R described above.

FIG. 5 is a partially schematic perspective view of a simple elliptical exercise machine 500 according to an embodiment of the invention. The machine body includes known mechanical linkages and controls to guide user motion. The elliptical further includes a left foot platform 70L and a right foot platform 70R; left and right fixed arm portions 72L, 72R; a left foot movement sensor 73L that includes a head mounted on an adjustable gooseneck support and a right foot movement sensor 73R that includes a head mounted on an adjustable gooseneck support. Foot pressure sensors 77L, 77R are located on the respective foot platforms. As is known, the elliptical machine may also include a left movable arm and a right movable arm. A Control Panel 10 of the type described above is provided at a convenient location.

FIG. 5A is a perspective view of another form of sensor head according of to an embodiment of the invention. The sensor head includes a motion sensor portion 73s and a LED light 73Q that can be used to provide the left and right flashes of steps 392L and 392R described above.

Figure 6:
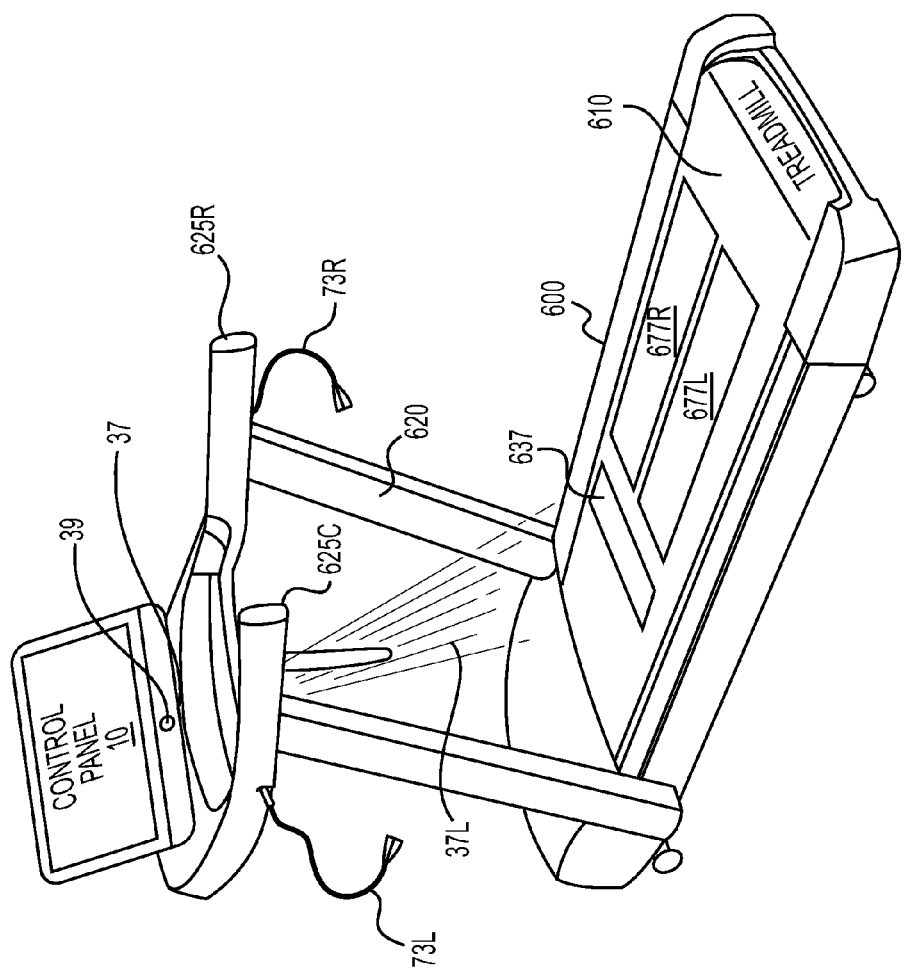
FIG. 6 is a partially schematic perspective view of a treadmill exercise machine according of to an embodiment of the invention.

FIG. 6 is a partially schematic perspective view of a treadmill exercise machine 600 according to an embodiment of the invention. As is known, the treadmill includes a body 600 that includes a base that houses a motor for driving a belt 610 that serves as a movable foot platform for exercise. An upwardly extending support 620 provides left and right arm portions 625L, 625R and a support for a Control Panel 10 of the type described above. The treadmill further includes a left foot movement sensor 73L that includes a head mounted on an adjustable gooseneck support and a right foot movement sensor 73R that includes a head mounted on an adjustable gooseneck support. Because the belt 610 moves and wears over time, it is not practical to provide pressure sensors on the belt. Instead, a left pressure sensitive region 677L and a right pressure sensitive region 677R are provided under the belt 610 to allow detection of foot pressure on the belt corresponding to left and right foot pressure. Characteristics of foot movement may also be detected by the time-of-flight sensors and camera 39 of the Control Panel 10.

When using a treadmill, it may be advantageous to provide lines of demarcation visible on the moving belt to guide user movement. With the computer controlled laser light bean projector 37 of the invention, it is possible to project images of lines of different colors onto the belt 610. The image of the lines of demarcation may be stationary or moving at a desired pace. As shown in FIG. 6, the laser light beam projector 37 projects a beam 37L that creates the image of a line of demarcation 637 on the belt 610.

The system and process described above facilitate sensory rhythmic time cuing in exercise with the use of foot platform (s) of cardio-fitness machines. Concepts of rhythm are interpreted to be understood as time organization whereas rhythm can be a symmetric, even pulse, as found in a metronome beat; also found in metered rhythm in which even pulses are grouped by accent into repeated groups of 2, 3, 4 and so on; and in rhythmic patterns consisting of a repeated musical phrase wherein the pulses or beats have different numerical ratio e.g., a long beat followed by a short beat half as long as the previous one, followed by two even shorter beats twice as short as the previous one etc. Audible pulse patterns are recurring rhythmic motifs found in musical phrases. Sensorimotor assimilation of regularly occurring beat events is learnable. An ability to time movement is conventional in human movements of clapping, finger tapping and head nodding. Rhythms therefore can fixate a response interval for the execution of movement. Rhythmic cues aid in regulating the brain and body ever more smoothly across durations of movement. And smoothing of acceleration and velocity enables an optimization of movement paths and trajectories in more advanced, goal directed, movement tasks.

The present invention provides a novel way of utilizing rhythms to trigger human beat perception and musical period matching during exercise. Because the elements of a song are a series of musical phrases and because at least a musical phrase is integral to the present invention, rhythmic stimuli, along with the inventive method, has the effect not of a randomized response, but of a precise kinematic rhythmic interval. Each successful sensorimotor synchronization of performance has the potential to improve the motor system's capacity for rhythmic entrainment.

Sensor detected movement on and with the foot platform (s) are exemplary of goal directed movement objectives where audible pulse stimuli at the beat events in the musical phrase cue performance methods to synchronize with them. Beat events guide movement patterns to be performed with a left or right extremity when a musical phrase begins, and to complete with the same side of the body when the music phrase ends.

Visible pause displayed in between the musical phrases (the pause display cue 30 at step 340) orients the user to begin a next performance of the GDM with the opposite extremity. A visual fade on the display screen precedes the user hearing an audible pulse. According to the user's preference, a touch controlled screen may alter the speed of the visual fade on the display screen and thus the timing of the audio out to the speaker or headphones. The visible pause may be reduced or optionally omitted as the user becomes proficient at performing GDM sequences more rapidly to several musical phrases playing in a row and in the event of GDM sequences being performed during the course of an entire song.

When the pause period ends (at step 350) the user is cued to reproduce the pattern again beginning on the opposite side. Performing patterns of left to right to left movement on and with the Fp, followed by right to left to right, (or vice versa) in time with a beat, evidences rhythmic sensorimotor synchronization whereby movement of the user's lower extremity on the Fp is detected by the sensors and correspondence (number of beats in a musical phrase and coincidence of detections within a pattern) is evaluated.

Such detections are made according to the method wherein at least a pattern of detection has been made and the sensor 73R has detected, the sensor 73L has detected, and the sensor 73R has a detected and whereas the same series of movement beginning on the left side are cued for a next performance where upon sensors 73L, 73R, 73L outputting signals, a visible signal successfully cued said performance.

Consequent to the above pattern of movement detection, a light cue from an LED within the sensor (73) provide immediate feedback that a correspondence (coincidence of an audible pulse (beat event) and coincidence of a detection within the movement pattern) was made.

The above detections may also correspond to the movement pattern's cessation e.g. the lack of the lower extremity entering the detection range of the exercise space and the unblocked sensor emitting a light beam. The visible signal making realized an interval cue for a next performance.

Additionally, movement may be detected by the sensors 73R, 73L, coincident with the light cues synchronized to the beginning and end of all musical phrases emitted from the interval lamp 35.

Light cues provide the user with immediate feedback that a coincidence between a beat in the musical phrase and a GDM was made. Lights cue the user in different ways according to the pattern of detection made. If an LED flashes during a performance of a pattern, the GDM detection is coincident with a beat in the musical phrase. This mode of feedback is obtainable in a user preference of repetitive cuing. When a beam flashes at the end of a pattern performance, the GDM detection is coincident with the last beat in the musical phrase, which also coincides with the completion of the GDM selected. This user preference is obtained in a user preference of interval cuing. Both forms of cuing are available to the user during a performance in addition to the system's interval cue (lamp 35), which is instructed to be synchronous with the first and last beat in any musical phrase selected. In either mode, Interval Cuing or Repetitive cuing, light cues correspond to the pattern of GDMs and the detections made while performing the pattern and the beginning and end of the music.

The following descriptions are exemplary of goal directed movement (GDM) sequences performed on and with the foot platforms of the cardio-fitness machines described above, namely an Adaptive Motion Trainer (AMT) 400, an Elliptical trainer 500, and a treadmill 600 whereby rhythmic sensorimotor synchronization is achievable according to the invention.

AMT

Following the pause period, at the start point in the first position GDM, a right foot platform 70R and left foot platform 70P of an AMT 500 are level with each other. In a second GDM a user engages the lower extremity to depress a Fp and third makes allowance for the Fp to return to the first position. The machine's mechanics force the Fp to rise. In this third GDM the user controls the level the Fp can rise to e.g. the start point whereby the Flash beam cue appears and the beats in the rhythmic phrase selected end simultaneous with the positioning of the Foot platform. Motion then resumes from the start point in the first position on the first beat in a musical phrase using the opposite foot platform. The user presses down on the Fp in time with the beat and the Fp rises to the next beat. The final sound signal i.e., the last of the beats in a musical phrase having a grouping of beats, corresponds to the cessation of movement e.g. the lack of foot motion and as such no detection is made and the unblocked sensor emits a visible signal.

The sensors 73R, 73L, 73R successively having detected a pattern of movement in the Fp's being depressed in tandem may signal an LED whereby the flashing light feeds back visual information for the performance to continue as specified (referred to as Repetitive mode where the sensor LED 73Q flashes at each GDM).

Also sensor 73R having detected twice in the interval corresponding to the first and last beats in a musical phrase, is synchronous with a light cue emitted from an interval Lamp 35 at the musical phrase's beginning and end. Laser Light Beam Projector 37 emits a flash beam simultaneous with detecting sensor 73R upon the determination that the sequence is complete by comparing specified number of GDM to detected GDM.

The sensors 73L, 73R, 73L successively having detected a pattern of movement in the Fp's being depressed in tandem may signal an LED whereby a flashing light feeds back visual information for the performance to continue as specified (referred to as Repetitive mode where the sensor LED 73Q flashes at each GDM).

Also sensor 73L having detected twice in the interval corresponding to the first and last beats in a musical phrase, is synchronous with a light cue emitted from an interval Lamp 35 at the musical phrase's beginning and end. Laser Light Beam Projector 37 emits a flash beam simultaneous with detecting sensor 73L upon the determination that the sequence is complete by comparing specified number of GDM to detected GDM.

Elliptical Trainer

In the start position the user exerts an uneven pressure on each Fp. A light cue (LED) appears respective to the Fp receiving more force, the rotation of which matches the beats in the rhythmic phrase (audio signal) selected. A GDM using the Foot platforms of an Elliptical Trainer is movement whereby at the start point in the first position GDM one Foot platform is in a low position closest to the floor and the adjacent Fp is in a high position furthest from the floor. The user motions the low Fp more aggressively in a manner similar to operating a skate board or similar motion controlled device where accelerated movement is achieved more so with one foot than the other. In this instance, one of the Fp's movement along its constrained path of motion is applied more pressure to in order to achieve a desired speed corresponding to the beats in the musical phrase. The Fp laterally opposite, although traveling at the same speed (due to the machine's constraints on motion performance while on board), is used to keep the user's balance. As such the users feet hold different positions during performance—the foot exerting the pressure is flush with the Fp the other is on tip toe.

The pressure sensors 77R and 77L detect rightward and leftward pressure on a foot platform respectively. For each rotation of a Right Fp, a pressure sensor 77R having detected, a comparator outputs successively the Fp's detection in comparison to the pressure sensor 77L and thus greater motion made with the right foot.

For each rotation of a Left Fp a pressure sensor 77L having detected, a comparator outputs successively the Fp's detection in comparison to the pressure sensor 77R and thus greater motion made with the right foot.

In addition the tight emitting sensors 73R and 731; detect rightward movement of a foot platform and leftward movement of a foot platform coincident to a beat in the musical phrase.

For each rotation of the Right Fp a light emitting sensor 73R having detected in conjunction with a pressure sensor 77R, a flashing light feeds back visual information for the performance to continue as specified (referred to as Repetitive mode where the sensor LED 73Q flashes at each GDM).

For each rotation of the Left Fp a light emitting sensor 73L having detected in conjunction with a pressure sensor 77L, a flashing light feeds back visual information for the performance to continue as specified (referred to as Repetitive mode where the sensor LED 73Q flashes at each GDM).

Laser Light Beam Projector 37 emits a flash beam simultaneous with detecting sensor 73L upon the determination that the sequence is complete by comparing specified number of GDM to detected GDM.

Laser Light Beam Projector 37 emits a flash beam simultaneous with detecting sensor 73R upon the determination that the sequence is complete by comparing specified number of GDM to detected GDM.

Also sensors 73R and 77R having detected movement during the interval coincident to the beats in a musical phrase, is synchronous with a light cue emitted from an interval Lamp 35 at the musical phrase's beginning and end.

Also sensors 73L and 77L having detected movement during the interval coincident to the beats in a musical phrase, is synchronous with a light cue emitted from an interval Lamp 35 at the musical phrase's beginning and end.

Treadmill

Simultaneously with a beat, the user synchronizes GDM of lower extremities on a Foot platform of a treadmill in a series of lunges. The exercise methods comprise a motor skill set of four GDMs. The pattern of weight shift in stride (walking) compares to the inventive subject matter of lunging as follows: in gait there are two steps in each stride, a total of two GDMs to pace the body forward; in a modification of stride, i.e. The lunge, there are four movements that pace the body forward. At the start point in the first position GDM both feet meet with the Foot platform parallel to each other. The first GDM resembles a giant step executed by shifting weight toward the front of the treadmill to achieve the lunge. In the second GDM, body weight is evenly shifted between the legs, knees bent in tandem. The third GDM, ascending, is activated by shifting weight from the rear leg to the front foot for propulsion of the rear foot to make the leg come forward. In the fourth GDM the leg swings forward so the rear foot can make contact with the Foot platform.

To achieve lunging on a treadmill in the order whereby the sensors 73R, 73L, 73R, 73L detect a pattern, an LED flashes a light cue and feeds back visual information for the performance to continue as specified (referred to as Repetitive mode where the sensor LED 73Q flashes at each GDM).

Laser Light Beam Projector 37 emits simultaneous with detecting sensor 73L upon the determination that the sequence is complete by comparing specified number of GDM to detected GDM.

Also sensors 73R and 73 L having detected movement during the interval coincident to the beats in a musical phrase, is synchronous with a light cue emitted from an interval Lamp 35 at the musical phrase's beginning and end.

To achieve lunging on a treadmill in the order whereby the sensors 73L, 73R, 73L, 73R detect a pattern, an LED flashes a light cue and feeds back visual information for the performance to continue as specified (referred to as Repetitive mode where the sensor LED 73Q flashes at each GDM).

Laser Light Beam Projector 37 emits simultaneous with detecting sensor 73R upon the determination that the sequence is complete by comparing specified number of GDM to detected GDM.

Also sensors 73L and 73R having detected movement during the interval coincident to the beats in a musical phrase, is synchronous with a light cue emitted from an interval Lamp 35 at the musical phrase's beginning and end.

As noted above, the Laser Light Beam Projector 39 (controlled by Laser Light Beam Control Engine 770) may be used to project an image of one or more lines of demarcation 637. The lines of demarcation may be of different colors and may appear stationary with respect to the machine base or moving at the speed of the belt. These lines are meant to increase the precision of the user's spatial orientation when performing GDMs on a treadmill.

In the embodiments described herein, the audio signal that is played back (at step 360) while the user performs a GDM sequence is a musical phrase. A musical phrase is a unit of musical meter that has a complete musical sense of its own, built from figures, motifs, and cells and combining to form melodies, periods and larger sections. A musical phrase is often equated to the length in which a singer or instrumentalist can play in one breath or, by some, as the smallest musical unit that conveys a more or less complete musical thought. Phrases vary in length and are terminated at a point of full or partial repose, which is called a cadence. Use of a musical phrase instead of larger musical structures is advantageous for new users because it is simpler to synch GDM with shorter compositions. Experienced users may be able to perform to more lengthy music structures, but doing so may require using a variety of GDM sequences. Thus, the ability to playback discrete musical phrases as the audio signal is an important aspect of the invention.

Using a single musical phrase as an audio signal to be played back requires detailed data concerning the beat events in the selected musical phrase. Such information could be obtained for selected musical phrases and stored either locally 130 or in network storage 55 accessible through the internet or cloud. However when beat event data files are not readily available, a beat detecting (extracting) engine 730 may be used to obtain beat event data for selected music files. The beat detecting engine 730 executes beat detectors against stored music files. Beat detectors execute against the music inputs from the PCM (musical phrase), identifying the beat event locations. Groupings of sound signals from the files stream as beat messages from the PCM. A beat message consists of a period time and a distance to the next beat event, both expressed in units of seconds. Beat messages output values from this detector source into bpm (beats per minute) and in this case, the number of beats in the musical phrase. The data provides the content for the Audible pulses (APs) at the beat events that are to coincide with movements on and with the Fp(s). In other words if during a performance the number of movements of and on the Fp(s) is coincident with the number of APs, movement will be judged to be at locations of the beat events (BE) in the music.

Figure 7:
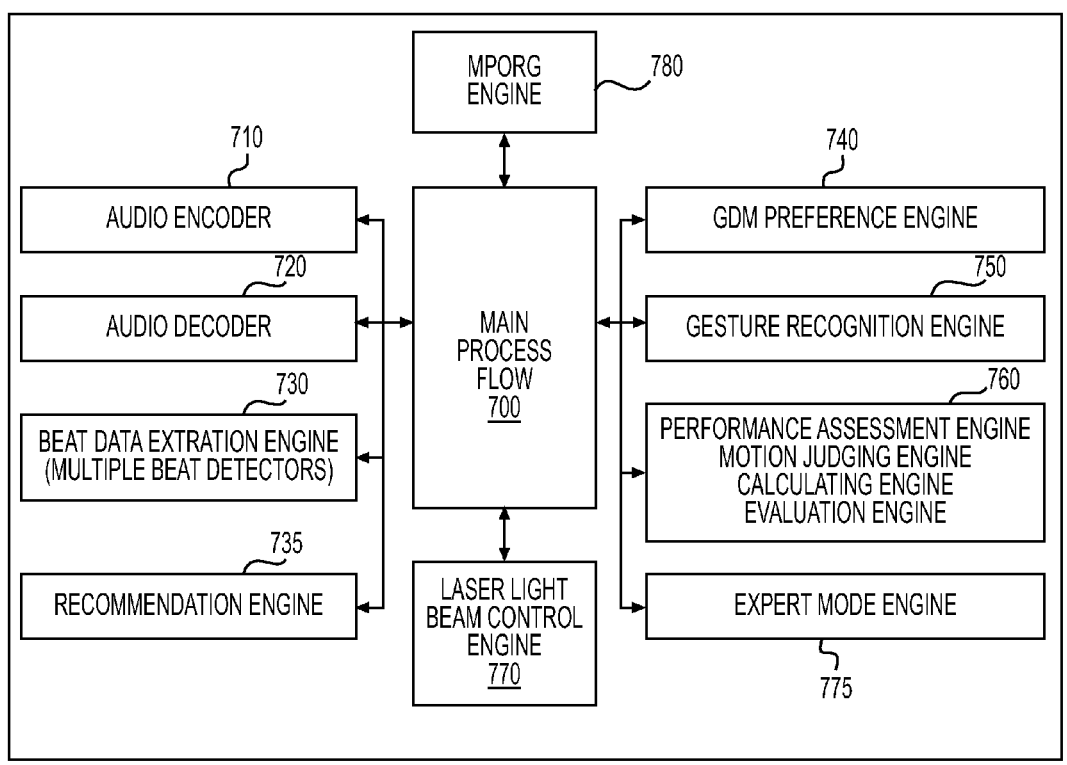
FIG. 7 is an overview of exemplary software architecture in an embodiment of the invention.

The CPU 100 preferably runs a motion judging engine (MJE) to judge whether the number of movements of the Fp (GDM performance) coincides with the number of Audible Pulses. As shown in FIG. 7, the motion judging engine may be part of the Performance Assessment Engine 760. The motion judging engine monitors (scans) all detection signals corresponding to the number of data positions related to beat events and movement of the Fp based on the detecting states of the sensors. Specifically the MJE monitors the number of movements and the variables noting their pattern: for example monitors how the sensors 73R, 77R, 73L, 77L enter their detecting states at a location of a beat event in patterns exemplifying movement made from left to right or movement from right to left i.e., 73R, 73L, 73R detecting simultaneous to 77R, 77L, 77R and then during the next musical phrase, 73L, 2L, 73L detecting simultaneous to 77L, 77R, 77L (or vice versa). In other words if a performance is in a pattern corresponding to the Audible pulses derived from the sound information (music inputs) and the sensors enter their detection states according to the pattern, the number of movements on and with the Fp is judged to correspond to the number of BE in the musical phrase.

A calculating engine calculates the number of correspondences (ratio) between the content information at the beat events (APs) and the detections. As shown in FIG. 7, the calculating engine may be part of the Performance Assessment Engine 760.

Before a GDM performance, data input from the music file is identified by the beat detecting engine (BDE). In a GDM performance the sensors 73R, 73L, output light cues and the CPU tabulates the detections. A difference is calculated from the number of music inputs reflected in the data (BE) and the number of sensor signals detected (movements on and with the Fp). The new value represents the ratio of beats to movements—an equal value reflecting a perfect score where by the number of detections is relative the number of AP stimuli. Evaluations are made by enumerating a sum value of detections by a left sensor, and a sum value of detections by a right sensor. The sums of relative detection signals and the sums of beat events are also used to evaluate results presented in a score.

An evaluating engine includes a score calculator. As shown in FIG. 7, the Evaluation Engine may be part of the Performance Assessment Engine 760. The score calculator gives a cumulative of the detections made relative to the assessment of user preferences for GDM. The pattern in which the sensors 73R and 73L make their detections at the BE provides further content for evaluation. A maximum of two detections, preferably by a same sensor, for the first and last beats of the musical phrase, result from user preferences for Interval cuing. The detections that follow are then made in the same manner by the sensor opposite. In other words if a performance originates with a right sensor detecting on the first beat, the performance originating with a left sensor detecting on the first beat will be considered the next performance.

In Interval cuing GDM performances will be evaluated as a correct movement pattern with a given number of cues per musical phrase resulting in standard value of 2. A sum may be derived from the number of beats in a musical phrase multiplied by the number of repeated musical phrases relative to the total number of detections. All sums may be presented as score information.

In the method of repetitive cuing, the pattern of detection relies on the motion sensors entering their states coincident with BE. In addition to the interval cues (Lamp 35) emitted at the beginning and end of the musical phrase, GDMs cause the sensors flash light (LED) and in addition to the detections received in response to the standard number of cues emitted by the Lamp 35. These additional detections increase the sum total of all detections. Results presented in repetitive cuing as score info may be derived from the number BE in the musical phrase, multiplied by the number of musical phrases repeated and the number of detections made.

GDM identified by an opposite sensor flagged as left or right dominant will be evaluated as a correct movement pattern. A GDM that is complete is assessed to contain the same number of GDM preferences in which case the light cue of a flash beam coincides with the cessation of movement at the end of the musical phrase and if the GDMs are coincident with the number of beats in the musical phrase the a same sensor detection may be made at the first and last beat of the phrase and will be also synchronous with the interval lamp cues provided by the system.

The results displayed and stored (at step 370) may include a score according instructed by the user preferences as follows:
  the beats in the musical phrase, the beats in the musical phrase multiplied by the number of musical phrases repeated
  the sum of right detections, the sum of left detections, the sum total of detections relative to the preferences for number of GDM sequences and the number GDMs in each sequence
  the beats in the musical phrase, the beats in the musical phrase multiplied by the number of musical phrases repeated and the ratio of detections in Repetitive cuing mode,
  the beats in the musical phrase multiplied by the number of musical phrases repeated and the ratio of detections in Interval cuing mode,
  (the total number of beat events×standard cues 2)

FIG. 7 is an overview of exemplary software architecture in an embodiment of the invention. The software controlling the main processes may be run in the CPU 100 or in special purpose microprocessors such as the Audio Processor 150 or Gesture Recognition Processor 139. As shown, the software includes the Main Process Flow 700, which is generally shown in FIG. 3. The software also includes an Audio Encoder 710, an Audio Decoder 720, a Beat Data Extraction Engine 730 (which may optionally include multiple beat detectors), a Recommendation Engine 735 for suggesting audio or GDM based on user performance, a GDM Preference Engine 740, Gesture recognition Engine 750, a Performance Assessment Engine 760, a Laser Light Beam Control Engine 770, Expert Mode Engine 775 and a MPORG Engine for coordinating functions related to multiplayer online role playing gaming through the network 50. The Performance Assessment Engine 760 may include subroutine for Motion Judging, Calculation and Evaluation. A separate engine may also be provided for processing foot pedal motion (step 390) and foot pressure signals. Naturally the functions performed in engines 710-780 could be incorporated into main process flow, but use of separate engines permits adaptation of commercially available solutions for functionality that is ancillary to the core functionality of the present invention. To the extent the specific processes for achieving specified functionality are not described here, there are commercially available solutions available such as audio encoders and decoders, for example.

Figure 8:
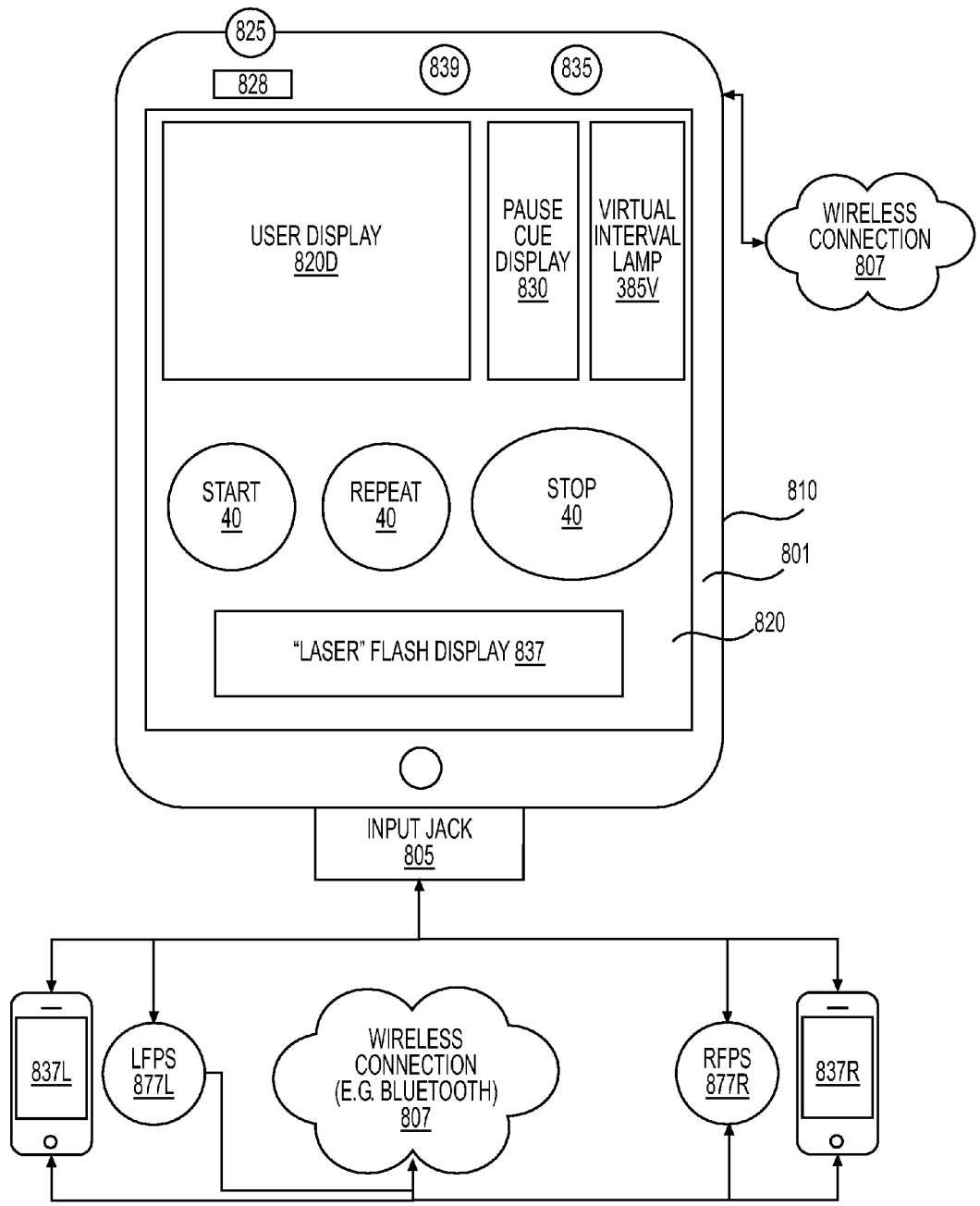
FIG. 8 is a schematic view of a general purpose multipoint touchscreen computing device adapted for use in the invention.
Figure 8A:
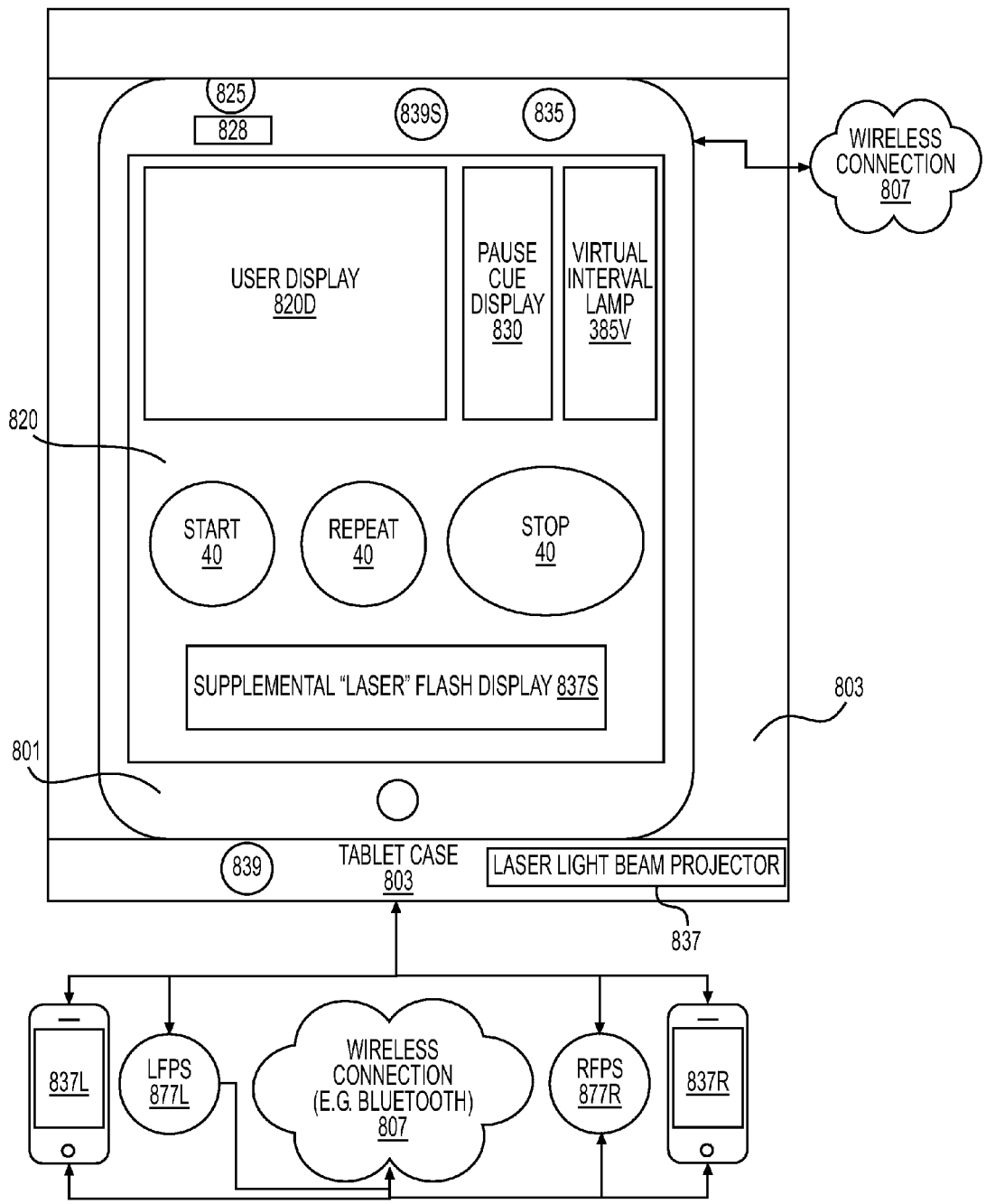
FIG. 8A is a schematic view of a general purpose multipoint touchscreen computing device with a casing providing additional hardware adapted for use in the invention.

As evident from the foregoing description, much of the functionality of the invention may be computer implemented. Thus, while the exemplary embodiments described above in connection with FIGS. 4-6 show a special purpose Control Panel 10 connected to the cardio fitness machine and associated hardware attached to portions of the cardio fitness machine, it is possible to implement the invention using more portable equipment. As shown in FIGS. 8 and 8A, for example, the invention may be implemented using a general purpose tablet computer or "smart phone" together with sensors that may be connected wirelessly (or wired) to the general purpose touch screen computing/communication device (tablet or smart phone).

As shown in FIG. 8, the general purpose computing/communication device 810 includes a casing 801 housing internal components and a multi touch screen 820 that covers most of the face of the device 810. The touch screen 80 is the primary user interface for operating the device. General purpose touch screen computers typically include components analogous to most of the components of the Control Panel described and shown in FIG. 2 (with the CPU being an acceptable substitute 100 for special purpose processors such as 139 and 150). Such devices use application software to cause the computer to perform tasks (applications) beyond the running of the computer itself. Such software is called software application, application or most commonly just an "app." The hardware in the typical device 810 is capable of executing an app directing the process flow of FIG. 3 and the other software engines shown in FIG. 7. Thus, the general purpose device of 810 could be used to run a app embodiment of the invention.

In the embodiment shown in FIG. 8, the hardware features found on the general purpose device are used to the extent possible. Thus, the audio jack 825 and speaker 828 are used as a substitute for the audio jack 25 and speaker 28 described above. A camera 839 may be used for some form of time of flight sensing (though a dedicated time of flight sensor and camera 839 in FIG. 8A is preferred) as an alternative to the camera 39 described above. The camera flash 835 may be used as alternative to the interval lamp 35 (or a virtual Interval lamp 835v could be displayed on the touch screen 820). The touch screen 820 could be used to display other components including the user display 820d; the pause cue display 830; a virtual "laser" flash display 837 and user selection buttons 40. The motion sensors 837L, 837R and pressure sensors 877L, 877R could be wirelessly connected to the device 810 through a wireless connection 807 or a wired connection using an input jack 805. The motion sensors 837L, 837R are detachable mountable to a surface of the cardio fitness machine. The pressure sensors 877L, 877R could be detachable mounted the cardio fitness machine as well, but it may be preferable to locate the sensors in a user's shoe. Motion sensors could also be attached to (Sewn into) user's apparel or bands worn by the user.

As described above, an embodiment of the invention may be implemented in a general purpose tablet or smartphone. Depending on the specific device, however, the available hardware may be sub-optimal. Where desired a special purpose protective case 803 may be used to both protect the device 810 and provide supplemental hardware to facilitate the present invention.

As shown in FIG. 8A, the device 801 is the same as described above in connection with FIG. 8. In this embodiment, however, the device 801 is encased in a separate case 803 that has, at least, a laser light beam projector 837 and a time of flight sensor and camera 839 built into the case 803. The components 837, 839 in the case are connected to the device 801 to provide enhanced hardware functionality that is closer to that found in the Control Panel 10 described above. The case 803 may also include one or more input jacks to allow the motion and pressure sensors to be connected by wire (as an alternative to the wireless connection 807). Other hardware components such as lamps, selection buttons and speakers can be provided in the case 803 as desired.

The present invention results in surprising improvements in exercise efficiency. The precise reasons for this synergistic increase is not yet certain, but it is believed that the present invention facilitates an exercise method that engages physiologically complex brain processes to shape and modulate brain and behavior and systems and methods for facilitating the method. Researchers have demonstrated that rhythm creates anticipation and predictability. Rhythm organizes time and rhythmic events are referenced and synchronized against underlying sensations of pulse patterns—pulses establish anticipation and predictability (audio beats are examples of pulse markings). The primary element in music that creates the perception of time is rhythm. Rhythm may enhance brain operations by providing structure and anticipation in time. Indeed, rhythm may be central to optimizing basic learning and perception processes. Motor response may be synchronized to an auditory rhythm and responding slightly ahead of time—within conscious perception of coincidence turns the task into a feed forward response.

Research suggests that music can uniquely engage the brain as a language of time, providing temporal structure to enhance learning and perception, especially in the areas of cognition, language and motor learning. Auditory rhythm is a powerful sensory cue that can regulate motor timing and coordination.

Rhythmic entrainment is linked to feed forward response. In the auditory mode, synchronization is an anticipatory response to an event that has not taken place, but whose precise occurrence time is known. Auditory rhythm can entrain the rhythmic motor responses—considering the nature of rhythm as a temporally predictable structure of timed events, responding ahead of the beat makes sense simply by maximizing the benefit of anticipation to programming the motor responses. As a result of the equidistant beat sequence, it is known to the brain when the beats will occur. Responding slightly ahead of time turns the task into a feed forward response a few milliseconds after the beat occurred, which provides feedback at a time when no correction of the response interval is possible. Receiving the beat feedback after the executed response gives appropriate sensory confirmation when corrections can be made for the next response cycle. Research suggests the existence of a central nervous system timing mechanism that helps regulate and control motor behavior. Support is found in the fact that humans are able to synchronize movement with external rhythmic sources as in clapping and dancing to music. Once synchrony of tapping to a metronome beat has been attained, the rate of tapping can be maintained after the metronomes stimulus has been removed. If we assume this mechanism has a role in controlling cyclic movement that is not driven by an external rhythm, we may expect that the consistency/variability of the timing of target contact will be a function of the precision of this internal timing system.

Visual cues are not as effective as auditory cues based on comparisons of visual cues and with auditory metronome cues possibly because rhythm accesses a central motor control system that, unlike visual cues, operates independently from peripheral mediators. Rhythmic activities inspire spontaneous growth of new neural circuits in the brain, improving physiological functions such as motor execution, and cognitive functions including memory and learning. The brain has several different rhythms known as Alpha, Beta, Delta and Theta waves, and there are also oscillating waves between the two hemispheres. As we age the rate of these hemispheric oscillation decreases and sometimes some parts of the brain develop abnormal or low oscillation rate, which can result in movement impairment or progressive cognitive deficit. The brain is equipped with music-specific neural networks, while auditory cues processed in flee brain differently for language and music with some overlapping regions especially when singing or listening to the lyrics on the music. The brain has distinctive features of neural systems supporting music and language while separating phonological phrases (combined with melody) that are processed as music bilaterally, from semantic sentences (processed as language) that occur more in the left hemisphere. Monotonic rhythmic cues, such as finger tapping or listening to the metronome has a bilateral effect on brain activation similar to variable rhythmic cues like listening or dancing to music, but unlike the general effect of music, monotone cues create specific associations with areas that support activities such as movements and cognitive functions. Bilateral brain activation with monotonic auditory cues has been documented to inspire spontaneous brain reorganization that can support improvement in movements and cognitive functions.

Accordingly, the invention facilitates rhythmic entrainment to achieve surprising improvements in the efficiency and effectiveness of exercise through rhythmic exercise. The present invention provides an exercise method engaging physiologically complex brain processes to shape and modulate brain and behavior and systems and methods for facilitating the method. The method preferably comprises a sequence of goal directed movements GDM (exercise routine) that is synchronized to rhythmic cues in a feed forward fashion that allows the user to anticipate the cues (feed forward) and optimize (smooth, make more precise and efficient) the entire range of exercise motion. As used in this context, "optimize" means "an optimal balance of expenditure of energy (cost) and useful motion (benefit) to achieve the most efficient and enjoyable exercise." Naturally, "optimize" is used in the real world context to suggest an improved cost/benefit balance that represents an improvement that can approach theoretical optimization. As used in this application, "Exercise" is the movement of joints to challenge muscles in different ways. An "Exercise Routine" is the topography of movement of joints designed to be repeated to maximize safety and muscle strength gains, i.e., the repeated movement of joints in a specific sequence, patterns and/or range to challenge muscles in different ways. In the context of this application, a GDM sequence could be considered a precision exercise routine. The complete sequence patterns and/or range of movement that is repeated may be referred to as a 'rep" or repetition. Performing the joint movements at the intended pace and in the intended sequence, pattern and/or range of movement is referred to as "precise movement," "exercise precision" and "precise form." "Exercise precision" is essential to optimal and efficient exercise. Failure to use precise form during a training set can result in injury or an inability to meet training goals—since the desired muscle group is not challenged sufficiently. The word "exemplary" is used herein to mean "serving as an example, instance, or illustration." Any aspect described herein as "exemplary" is not necessarily to be construed as preferred or advantageous over other aspects.

As described, the invention provides a method, system and equipment to facilitate goal directed movement. Through use of the method, system and equipment, the user will experience an enhanced GDM with improved results and increased efficiency. In accordance with another important aspect of the present invention, the improved user experience creates business opportunities that can benefit the user, the system provider and vendors—especially as users become more accustomed to use of the invention and advance to more sophisticated audio signals and/or GDM sequences.

In particular, the method, system and equipment of the present invention are designed to motivate the user to identify and make available information about themselves including music preferences and demographic information that could include physical attributes (age, gender, height, weight), and geographic location. In addition, the method, system and equipment can capture the user's performance pattern, efficiency and preferences. Moreover, the method, system and equipment can be designed such that the user is encouraged to experience sensory impressions (such as viewing images on a screen) for much of the duration of the GDM session. By collecting and processing all of this available information it is possible to achieve utility that cannot be otherwise achieved.

It is possible to provide add on's such as games, reward systems (real or virtual) or feedback/exercise history sites on the internet that will encourage a user to register and thus provide even more demographic information.

By way of example only, using the method, system and equipment of the invention in communication with other users through the internet or other networks or clouds, it is possible to:

Compare a user's performance to other similar users.

Compare a user's performance with musical phrases, melodies or songs of one "demographic type" to performance with songs of another "demographic type" and make suggests as to the best type of music for THAT user [demographic type as used here means the beat rate and/or other statistics of the music that can be compared].

Identify music that the user is most likely to perform well to, based on the users performance when using different types of music and an analysis of the "demographics" of music the user has used in the past.

Allow the user to purchase music [musical phrases, melodies or songs].

Identify advertising demographics of the user based on musical preferences, demographic information provided by the user (to use the equipment or register for a "add ons" offered on the web—using any or all of the available information, it is possible to display advertising sensory impressions to the user throughout the GDM session—for example, visual impressions on a display screen or audio impressions. Because the user is a content, but "captive" audience for an extended period and because of the insight into the particular user that can be obtained from all information collected about the user (especially musical preference, which is something not often coupled with the other types of information collected, it is possible to target advertising very accurately.

In this sense, the method, system and equipment of the invention make it possible to bring together knowledge of a user's musical preferences (which is indicative of certain user traits) with other information that is available to enhance advertising.

Other embodiments of the invention are naturally possible the wide range of available equipment for sensing applied pressure and motion. The sensors 37, 77, 837, 877 and the may be designed and arranged to detect motion in a sensing area include the range to the left and right above the users waist The system of the invention may also be operated in an EXPERT mode. The EXPERT mode may be coordinated using a Expert Mode Engine 775 that repurposes system components so that, in EXPERT mode, the audio signal is played and the system records the user's GDM as detected by the sensor system and stores the recorded sequence as a new GDM. In this way a preferred GDM sequence may be associated with an audio signal. This EXPERT mode allows an experienced user to easily create GDM sequences for a variety of musical phrases or other audio signals. The EXPERT mode could also be used by a less experienced user to store the GDM sequence the "created" in connection with a favorite musical phrase or other audio signal. The system can assess the new GDM sequence using the performance assessment engine 760, for example. A new GDM sequence for a particular musical phrase or audio signal that is created using the EXPERT mode may be stored (locally 130 or on network storage 55) and made available for use by others, if desired. It may be desirable to identify (and perhaps limit storage for use by others only to) those GDM sequences having a comparatively high performance assessment, i.e., GDM sequences that are appropriately synched to the audio signal. Using the EXPERT mode, users (especially experienced users) could create an eco-system of user created GDM sequences associated with a wide variety of music. Such new offerings could be sold or otherwise made available to improve the user experience.

Although the detection of the movement patterns herein described are presently novel these and other movement patterns known to the inventor may be embodied in other forms of technology as CPU input i.e. as coordinates in software data that may be used as stored detection information in addition to the sound information so that a user may follow a pattern more precisely whereby light emissions for all known patterns to the inventor display instructively to the user for reproduction of said patterns according to musical phrases and songs known to the user.

Although the detection of movement is herein described to be used in conjunction with audible stimuli, visual stimuli acquired in the instance of the above description of patterns known to the inventor becoming realized as coordinates and may be included as challenging to the user. User performances may be compared to more advanced performances for scoring in an MultiPlayer Online Role Playing Game [MPORG] where participants choose avatars to represent, for example, their physical attributes and earn points to change their physiques by performing the exercise first and uploading their own coordinates afterward to achieve a more enhanced physical attribute Players can buy such attributes but it should be costly to play. If this functionality is desired a conventional MPORG engine 780 may be used to control system functionality and interface with the network 50.

As noted above, the sensor system of the invention may include sensors embedded (or otherwise attached to) footwear, apparel and other athletic wear (anything worn by the user). In this context, the use of apparel specific to the promotion of enhanced methodology may be included in the motion sensor system and method of rhythmic cuing. Footwear and athletic wear that embodies the present invention whereby the sensors are embedded within the apparel that enable detections to be made and seen as visible cues further expanding the possibilities for make and use.

The system could support sales of music (musical phrases and other audio signals), custom GDM sequences and other tools to facilitate use of the invention. A motion sensor system and method of rhythmic cuing may allow the user to purchase music identified as suitable of certain user traits, with other information that is available to promote information sharing with other domains outside of the proprietary domain such as health care networks, agencies and all those dedicated to public interests. In particular, the particular motion patterns and rhythm of a user—detected through use of the invention—can be used to create a GDM profile for that user. Based on the GDM profile (stored locally 130, on network storage 55 or on a memory card 23 or wireless tag such as a RFID chip, for example) the system may recommend music and/or GDM sequences for the user. The processing for this recommendation engine 735 could be performed in the CPU or in a separate recommendation engine processor. Diverse musical phrases like a juke box, categorized according to the beats in the musical phrase (and possibly recommendation) may be presented for sale and/or use to the user through the control panel 10, 810.

Positron emission tomography (PET) brain imaging (or other imaging techniques) could be used to determine the extent to which (and provide evidence that) neuronal arousal with precision execution of motion increases with a rhythmically cued activity, evidencing that plasticity is made possible in brain tissue, in addition to growth in muscle tissue. PET brain imaging may enhance the evidence with before and after results and offer more to the fields of study in audio sound processing in humans and neurology.

Improvements in beat detection will make it more practical to offer more options for a listener to base his impressions on including note onsets, drumbeats and patterns, and harmonic changes. To this end, a plurality of beat detectors may be launched simultaneously (in beat detection engine 730, for example) to improve the overall accuracy and experience of a system and method of the present invention. A plurality of monitors aggregating information from multiple detectors generates a more advanced beat tracking response over an individual detector operating independently. This improvement in digitizing music will benefit usage of the present invention and the ability to achieve the objective of performing goal directed movements in response rhythmic cuing.

The embodiments described herein are exemplary and not intended to be exhaustive of the applications of the systems and methods of the invention.

What is claimed is:

1. A cardio fitness machine that generates sensory cues to guide a user in performing goal directed movements (GDM) in a GDM sequence in coordination with rhythmic elements of an audio file, where the GDM sequence comprises a plurality of distinct GDMs including an initial GDM at initiation of the GDM sequence and a final GDM at completion of the GDM sequence and the audio file comprises at least one musical phrase that contains at least three beat pulses, the cardio fitness machine comprising:
   a control panel configured to receive user selections including at least a user selection of an audio file comprising at least one musical phrase that contains at least three beat pulses and a user selection of a GDM sequence comprising a plurality of distinct GDMs; wherein the control panel includes memory for storing data including stored audio file data and stored GDM sequence data; the control panel is further configured to load stored audio file data in response to the user selection of the audio file and load stored GDM sequence data in response to the user selection of the GDM sequence; determine a timing and location of the beat pulses in the user selected audio file and identify the plurality of distinct GDMs including a sequence of right foot movements and left foot movements in the user selected GDM sequence; the control panel further comprising an audio processor configured to obtain beat information for the user selected audio file and playback the user selected audio file, the user selected audio file playback having an initiation and a conclusion;
   at least one foot support portion, the at least one foot support portion supported on the cardio fitness machine and configured for continuous movement along a known path;
   a sensor system, the sensor system comprising a first sensor positioned to detect only movements in an exercise space associated with a right side of the user and a second sensor positioned to detect only movements in an exercise space associated with a left side of the user; wherein the sensor system is configured to detect the right foot movements and the left foot movements of the user and distinguish between the detected right foot movements and the left foot movements,
   wherein the control panel is further configured to receive signals from the first and second sensors indicative of a sequence of detected movements in the exercise space associated with the right and left side of the user and compare the sequence of detected movements to the user selected GDM sequence; and
   a plurality of sensory cue generators controlled independently of one another and configured such that a first sensory cue generator generates a non-audio sensory cue at the initiation and conclusion of the user selected audio file playback and a second sensory cue generator generates a sensory cue at the initiation and conclusion of the user selected GDM sequence.

2. The cardio fitness machine of claim 1, wherein the at least one foot support portion comprises two moveable foot support platforms; the two moveable foot support platforms are moveable with respect to one another.

3. The cardio fitness machine of claim 2, wherein the cardio fitness machine is an elliptical trainer machine.

4. The cardio fitness machine of claim 2, wherein the cardio fitness machine is an Adaptive Movement Trainer (AMT) machine.

5. The cardio fitness machine of claim 1, wherein the control panel is configured to compare timing of the detected right foot movements and left foot movements with the determined timing of the beat pulses in the user selected audio file and provide feedback to the user.

6. The cardio fitness machine of claim 5, wherein comparing the timing of the detected right foot movements and left foot movements with the determined timing of the beat pulses in the user selected audio file comprises comparing a number of beat pulses in the user selected audio file to a number of the detected right foot and left foot movements of the user.

7. The cardio fitness machine of claim 1, wherein the control panel is configured to determine the timing and location of the beat pulses in the user selected audio file using the loaded stored audio file data.

8. The cardio fitness machine of claim 1, wherein the control panel is configured to determine the timing and location of the beat pulses in the user selected audio file using a beat detection engine configured to extract beat data from the user selected audio file.

9. The cardio fitness machine of claim 1, wherein the sensor system comprises a time of flight sensing system.

10. The cardio fitness machine of claim 1, further comprising a wireless communication processor configured to receive signals from a plurality of wireless sensors worn by the user to detect user movements in performing the user selected GDM sequence.

11. The cardio fitness machine of claim 1, further comprising a data recording system configured to record and store the right foot and left foot movements of the user as detected by the sensor system during the user selected audio file playback as a new GDM sequence.

12. The cardio fitness machine of claim 1, wherein the first sensor and the second sensor are motion sensors.

13. The cardio fitness machine of claim 1, wherein the at least one foot support portion comprises two foot support portions that are moveable relative to one another, wherein one of the two foot support portions support the right foot of the user and the other one of the two foot support portions support the left foot of the user, the two foot support portions each comprising at least one pressure sensor, each of the at least one pressure sensor is configured to detect a pressure applied by the right foot and the left foot of the user, and provide signals that allow the sensor system to distinguish between the right foot pressure and the left foot pressure.

14. The cardio fitness machine of claim 1, wherein the control panel is further configured to provide a visible pause cue during a pause period prior to the user selected audio file playback and control the user selected audio file playback and the plurality of sensory cues such that when the pause period ends, a first beat in the user selected audio file becomes audible which is synchronous with the non-audio sensory cue generated by the first cue generator at the initiation of the user selected audio file playback, and wherein upon completion of the user selected audio file playback, which is synchronous with the non-audio sensory cue generated by the first cue generator at the conclusion of the user selected audio file playback, the control panel determines, according to user preference stored instructions, whether to repeat the user selected audio file playback and, if so, a new pause period is initiated, and if not, a GDM performance assessment procedure is initiated during which, the control panel is configured to
   monitor the user's movements by receiving a foot movement signal, determining if the foot movement signal came from the first sensor or the second sensor, and determining whether the foot movement signal received is the first foot movement signal of the user selected GDM sequence and, if so, flagging the user selected GDM sequence according to whether the foot movement was the left foot movement or the right foot movement;

store separate counts of the left foot movements and the right foot movements and determining whether the user has completed performing the user selected GDM sequence by comparing the counts of the left foot movements and the right foot movements to a number of beat pulses in the user selected audio file; and wherein the second sensory cue generator generating the sensory cue at the conclusion of the user selected GDM sequence in response to determining that the user has completed performing the user selected GDM sequence.

15. A portable audio file playback and cue generating device for use in association with a cardio fitness exercise equipment having at least one foot support portion supported on the cardio fitness equipment and configured for continuous movement along a known path and a sensor system comprising a right sensor positioned to detect and generate a signal in response to only movements in an exercise space associated with a right side of a user and a left sensor positioned to detect and generate a signal in response to only movements in an exercise space associated with a left side of a user, wherein the portable audio file playback and cue generating device is configured to generate sensory cues to guide users in performing a sequence of known goal directed movements (GDM) in a GDM sequence in coordination with rhythmic elements of the audio file where the GDM sequence comprises a plurality of distinct GDMs including an initial GDM at initiation of the GDM sequence and a final GDM at conclusion of the GDM sequence and the audio file comprises at least one musical phrase that contains at least three beat pulses, the portable audio file playback and cue generating device comprising:

a control panel configured to receive user selections including at least a user selection of an audio file comprising at least one musical phrase that contains at least three beat pulses and a user selection of a GDM sequence comprising a plurality of distinct GDMs to be performed on a cardio fitness exercise equipment; the control panel configured to determine a timing and location of beat pulses in the user selected audio file and identify the plurality of distinct GDMs including a sequence of left foot movements and right foot movements in the user selected GDM sequence; wherein the control panel is further configured to receive signals from the right and left sensors indicative of a sequence of detected movements in the exercise space associated with the right and left side of the user and compare the sequence of detected movements to the user selected GDM sequence; the control panel further comprising an audio processor configured to obtain beat information for the user selected audio file and playback the user selected audio file, the audio file playback having an initiation and a conclusion; and a plurality of sensory cue generators controlled independently of one another and configured such that a first sensory cue generator generates a non-audio cue at the initiation and conclusion of the user selected audio file playback and a second sensory cue generator generates a sensory cue at the initiation and conclusion of the user selected GDM sequence.

16. The portable audio file playback and cue generating device of claim 15, wherein the control panel is further configured to provide a visible pause cue during a pause period prior to the user selected audio file playback and control user selected audio file playback and the generation of sensory cues such that when the pause period ends, a first beat in the user selected audio file becomes audible, which is synchronous with the non-audio sensory cue generated by the first cue generator at the initiation of the user selected audio file playback and wherein upon completion of the user selected audio file playback, which is synchronous with the non-audio cue generated by the first cue generator at the conclusion of the user selected audio file playback, the control panel determines, according to user preference stored instructions, whether to repeat the user selected audio file playback and, if so, a new pause period is initiated; and if not a GDM performance assessment procedure is initiated during which the control panel is configured to monitor the user's movements by receiving a foot movement signal, determining if the foot movement signal came from the right sensor or the left sensor, and determining whether the foot movement signal received is the first foot movement signal of the user selected GDM sequence and, if so, flagging the user selected GDM sequence according to whether the foot movement was a left foot movement or right foot movement, store separate counts of the left foot movements and the right foot movements and determining whether the user has completed performing the user selected GDM sequence by comparing the counts of the left foot movements and the right foot movement to a number of beat pulses in the user selected audio file; and wherein the second sensory cue generator generating the sensory cue at the conclusion of the user selected GDM sequence in response to determining that the user has completed performing the user selected GDM sequence.

* * * * *